(12) United States Patent
Shantha

(10) Patent No.: US 9,254,219 B2
(45) Date of Patent: Feb. 9, 2016

(54) SNORING AND OBSTRUCTIVE SLEEP APNEA PREVENTION AND TREATMENT DEVICE

(76) Inventor: Totada R. Shantha, Stone Mountain, GA (US)

( * ) Notice: Subject to any disclaimer, the term of this patent is extended or adjusted under 35 U.S.C. 154(b) by 811 days.

(21) Appl. No.: 13/485,951

(22) Filed: Jun. 1, 2012

(65) Prior Publication Data

US 2012/0234331 A1   Sep. 20, 2012

(51) Int. Cl.
*A61F 5/56* (2006.01)

(52) U.S. Cl.
CPC ........................................ *A61F 5/566* (2013.01)

(58) Field of Classification Search
CPC ............ A61F 5/56; A61F 5/566; A61C 7/145
USPC .......................... 433/6, 93, 140; 128/848, 860
See application file for complete search history.

(56) References Cited

U.S. PATENT DOCUMENTS

| | | | | |
|---|---|---|---|---|
| 4,669,459 A | * | 6/1987 | Spiewak et al. | 128/848 |
| 5,915,385 A | * | 6/1999 | Hakimi | 128/848 |
| 6,467,484 B1 | * | 10/2002 | De Voss | 128/848 |
| 7,823,590 B2 | * | 11/2010 | Bibi et al. | 128/206.29 |
| 7,918,228 B2 | * | 4/2011 | Smernoff | 128/846 |
| 2003/0188752 A1 | * | 10/2003 | Zirafi et al. | 128/848 |
| 2006/0118120 A1 | * | 6/2006 | Russo | 128/207.14 |
| 2008/0041396 A1 | * | 2/2008 | Lucker | 128/845 |

FOREIGN PATENT DOCUMENTS

JP   2008-183388 A   *   8/2008

* cited by examiner

*Primary Examiner* — Nicholas Woodall
*Assistant Examiner* — Camtu Nguyen
(74) *Attorney, Agent, or Firm* — Mark David Torche Patwrite LLC

(57) ABSTRACT

The present invention is a safe, inexpensive, easy to use and effective anti-snoring and anti-sleep apnea treatment device. The device has a vertical and horizontal bar. The horizontal bar is placed inside the mouth, behind or between the molar teeth with palatine and tongue shelves to prevent snoring and movement of the tongue backwards. The device is tethered to the hard palate by vacuum cups to prevent the movement of the tongue backwards during sleep to prevent sleep apnea. The proximal end of the vertical bar is anchored to string at the distal end with hook and loop fabric closure adhesive attachment and to the lips outside the mouth to prevent the accidental swallowing and aspiration of the device; and at the same time holds the tongue and device firmly in the mouth. The device is provided with canula with three way stopcocks to deliver supplemental oxygen and therapeutic agents.

8 Claims, 19 Drawing Sheets

SNORING AND OBSTRUCTIVE SLEEP APNEA PREVENTION AND TREATMENT DEVICE

FIELD OF THE INVENTION

The present invention relates to a device used for treatment of patients suffering from snoring and obstructive sleep apnea (OSA) syndromes. These conditions are due to a breathing malfunction occurring during sleep that results in the narrowing and/or obstruction of the upper respiratory passages. During the therapy using our device, the palatine and tongue muscles are splinted, supported, and largely immobilized to prevent the palate from vibrating with prevention of obstructive sleep apnea. This device prevents the tongue falling back in the mouth during sleep. The current invention relates to anti snoring and anti obstructive sleep apnea (OSA) devices and their methods of use.

BACKGROUND OF THE INVENTION

The tongue and soft palate play a major role in the production of snoring and obstructive sleep apnea, and their participation is needed to causes these symptoms to exist. Hence, it is imperative to have knowledge about these structures, which play a major important role in snoring and obstructive sleep apnea. Most of us do not think of snoring as something to be overly concerned about. However, frequent, loud snoring may be a sign of sleep apnea, a common and potentially serious disorder in which breathing repeatedly stops and starts as you sleep. These breathing pauses during sleep apnea last between 10 to 20 seconds and can occur up to hundreds of times a night.

Although sleep apnea is treatable, it often goes unrecognized. Untreated sleep apnea can be dangerous and detrimental to your health, so it's important to see a doctor if you suspect that you or a loved one might have it. Read on to learn the warning signs of sleep apnea, how to distinguish it from normal snoring, the medical treatments available, and what you can do to help yourself.

The tongue is a muscular-neuro-vascular body on the floors of the mouths of most vertebrates. It maneuvers food for mastication and is the primary organ of taste, through papillae and taste buds that cover the surface of the tongue. The tongue is kept moist by saliva and mucous glands of the mouth. It is supplied with nerves, lymphatics, and blood vessels. In humans, a secondary function of the tongue is phonetic articulation. The tongue serves as a natural means of cleaning one's teeth by its all-directional movement capacity. In mammals (dogs, cats and other animals), the tongue has a rough surface which is used to clean the fur and body. A dog's tongue acts as a heat regulator.

The average length of the human tongue in adults from the oropharynx to the tip is 10 cm (4 inches). It has 5 intrinsic muscles (superior, inferior, longitudinal, transverse & vertical) within the tongue that are not attached to any bone where the 4 extrinsic muscles are attached to the bones below the tongue. They are the genio, hyo, stylo, palato-glossus muscles. The primary blood supply to the tongue is from the lingual artery, a branch of the external carotid artery. There is a secondary blood supply to the tongue from the tonsillar branch of the facial artery and the ascending pharyngeal artery.

The underneath of the front of the tongue is called the sublingual region where the oral mucosa is very thin with a rich plexus of veins. This sublingual region is used as route of administration of many therapeutic agents. For example, this is the distinct expedient and efficacious route of administration of nitroglycerin to a patient suffering chest pain from angina pectoris. This medicine would be ineffective if swallowed.

The tongue is one of the most active skeletal muscles masses in the body, used from the minute one wakes up to the time one goes to sleep. Hence, the tongue is constantly subjected to trauma, whether intended or unintended. The tongue is constantly moving while eating, drinking, and talking as well as during other facial activities. Hence, the tongue is subject to trauma by the teeth and the physical forces of cold and hot temperature of substances as well as exposure to different chemicals consumed like alcohol, acids, alkalis and toothpaste, etc., which play a role in affecting the tongue and palate.

The tongue is supplied by many sensitive nerves, which can cause the gag reflex from a foreign object. Taste sensation for the anterior ⅔ of the tongue is supplied by the Facial nerve (Chorda tympani, CN VII). General sensation of the anterior ⅔ is supplied by the Lingual nerve which is a branch of V3 of the Trigeminal nerve CN V. Taste as well as general sensation for the posterior ⅓ is supplied by the Glossopharyngeal nerve (CN IX). All intrinsic and extrinsic muscles of the tongue are innervated by the Hypoglossal nerve (CN XII), except for one of the extrinsic muscle, palatoglossus that is innervated by CN X of the pharyngeal plexus. The internal laryngeal nerve, a branch of the vagus nerve, supplies the posterior part of the tongue. The tongue plays a primary role in the production of obstructive sleep apnea.

The palate forms the roof of the mouth, made up of the hard palate in front, and the soft palate behind. The hard palate formed by the palatine processes of the maxilla and the horizontal plates of the palatine bone. Behind, it is continuous with the soft palate. The upper surface of the hard palate forms part of the floor of the nasal cavity lined by ciliated epithelium.

There are five pairs of palatine muscles of the soft palate involved in the movement of the palate and uvula, which can participate in production of snoring. They are 1 Tensor palati; 2. levator palati 3. Palatopharyngeus from the upper surface, 4. With the uvular muscles within the upper surface. 5. Palatoglossus from the lower surface. The flexible skeleton for the soft palate is due to the aponeurosis of Tensor palati muscle.

It is the soft palate along with the tongue and oro-laryngopharynx which plays a role in snoring and obstructive sleep apnea. The soft palate is suspended from the posterior border of the hard palate, extends downwards, and backwards between the oral and nasal parts of the pharynx. The soft palate consists of mucous membrane enclosing an aponeurosis, muscular fibers, vessels, nerves, lymphoid tissue, and mucous glands. Its superior border is attached to the posterior margin of the hard palate, and its sides are blended with the pharynx. Its inferior border is free, and that is what contributes to snoring. The uvula is a small conical form which hangs from the middle of its lower border where there are two curved folds of mucous membrane, which contain muscular fibers (palatoglossal arch), and extend laterally and downwards from each side of the base of the uvula. A thin, firm, fibrous lamella, termed the palatine aponeurosis, supports the muscles and gives strength to the soft palate, which is attached to the posterior border of the hard palate and to the inferior surface of the hard palate behind the palatine crest. The muscles of the palate include a levator and a tensor of the palate. The muscles are underlying in the palatoglossal and palatopharyngeal folds which extend into the palate itself and the muscle of the uvula with the exception of the tensor veli palatine. The flexible frame for the soft palate is due to the aponeurosis of Tensor palati muscle. The muscles are innervated by the mandibular nerve of the soft palate and are supplied by nerve fibers which leave the medulla in the cranial part of the accessory nerve which reach the pharyngeal plexus via the vagus nerve.

Snoring, hypopnea and obstructive sleep apnea (OSA) are caused by the vibrating soft palate; soft tissue of the nasal and oral pharynx, relaxed tongue moving backwards towards the oral and laryngeal pharynx which blocks the air passageway through the pharynx, or lingual compartment during sleep obstructing air passage through the naso, oro and laryngpharynx. Other causes include: the loose tissue within the mouth cavity including the flaccid tongue, the pharyngeal folding, tonsillar pillars, and the muscular uvula with the soft palate-called the pharyngeal arch that has a propensity to vibrate as tidal air flows past narrow air passages during sleep causing snoring and obstructive sleep apnea.

Snoring is an inspiratory sound, which arises in the course of a person's sleep due to the narrowing of the naso, oro, and laryngo-pharyngeal airway with inspiratory airflow in the narrow passages. The sounds of snoring are generated by vibration of soft tissues of oropharynx such as the soft palate, uvula, tongue, lips, the posterior faucial pillars of the tonsils, pharyngeal folds, posterior, and lateral pharyngeal wall and epiglottis in the upper airway, however, the soft palate and the uvula are the main culprits (FIGS. 1, 2, 3, 4).

Many causes for the narrowing of the nasal pharyngeal airway (FIG. 3, 4) during sleep exist besides the flaccid soft palate and the tongue role. People who snore rarely make snoring sounds when breathing while awake in the same position that is associated with snoring when asleep (FIGS. 1, 2). The reason being, that the person when awake has watchful control of various muscles of the upper airway that prevent the vibrations that cause snoring to occur (FIG. 1). During sleep, the motor neurons that control skeletal muscles are inhibited from sending the instructions (to make them active) that increase the tone of these muscles. This physiological process in sleep results in flaccid muscles that permit soft tissue to sag and collapse into the pharyngeal wall that results in snoring with OSA strikes (FIGS. 2, 3).

Up to 45% of all adults snore sporadically with about 25% being constant snorers. It is known that snoring increases with advancing age. This has been observed that about 50% of men and 40% of women are habitual snorers by the age of 60 (Lugaresi et al, "Snoring: Pathogenic, Clinical and Therapeutic Aspects", Reported in Principles and Practice of Sleep Medicine (Kryger et al, Editors (1989) at pp. 494-500). There are estimates of 28 million people suffering from OSA in USA.

One needs to discriminate the difference between non-obstructive snorers (FIG. 2) from the obstructive sleep apnea snorers (FIG. 3) and hypopnea (FIG. 2). Hypopnea is a medical term that involves episodes of shallow breathing or an abnormally low respiratory rate. This may not be due to naso-oro-laryngo-pharyngeal airways. This differs from sleep apnea in that there remains some flow of air. Hypopnea events may happen while asleep or while awake. It's abnormally shallow breathing lasting at least ten seconds. In the context of diagnosis and treatment of sleep disorders, a hypopnea event is not considered to be clinically significant unless there is a 30% or greater reduction in air flow lasting for 10 seconds or longer with an associated 4% or greater desaturation in the person's oxygen levels, or it results in arousal or fragmentation of sleep. During hypopnea, there is airflow, through a much-reduced level, which leads to not getting enough oxygen. The apnea-hypopnea index or respiratory disturbance index (AHI) is an index of severity that combines apneas and hypopneas. Combining them both gives an overall severity of sleep apnea including sleep disruptions and oxygen desaturation (a low level of oxygen in the blood).

An apnea index or AI shows the average number of apneas per hour of sleep. A hypopnea index or HI shows the average number of hypopneas per hour of sleep. An apnea and hypopnea index or AHI shows the average number of apneas and hypopnea per hour of sleep. Some doctors use the term of respiratory disturbance index or RDI, instead of AHI. The apnea-hypopnea index calculated by dividing the number of apneas and hypopneas by the number of hours of sleep. AHI values are categorized as 5-15 Mild, 15-30 Moderate, and above 30 listed as Severe. Example: Apnea+Hypopnea divided by actual sleep time, and then multiply by 60. 200 Apnea 200 Hypopnea=400 Total Events; 420 Actual Sleep time (7 hours). Divide 400 by 420=0.95×60 (minutes per hour)=57 AHI (Severe OSA).

The physiological terms used to describe various types of breathing associated with snoring and obstructive sleep apnea breathing difficulties are as follows. Eupnea—normal breathing; Apnea—absence of breathing; Bradypnea—decreased breathing rate; Dyspnea or shortness of breath—sensation of respiratory distress; Hyperaeration/Hyperinflation—increased lung volume; Hyperpnea—fast and deep breathing; Hyperventilation—increased breathing that causes $CO_2$ loss; Hypopnea—slow and shallow breathing, Hypoventilation—decreased breathing that causes $CO_2$ gain, and Labored breathing—physical presentation of respiratory distress. Obstructive sleep apnea (OSA) is due to complete blockage of air to the larynx due to mechanical soft tissue blockage (FIG. 3) by Naso-Oro-laryngo-pharyngeal tissue.

TYPES OF SLEEP APNEA: There are three types of sleep apnea. They are as follows:

1. Obstructive sleep apnea (OSA) is the common form of the condition when the tissues of the naso-oro-laryngeal-pharynx obstruct breathing during sleep. These pauses in breathing are called apneas (literally, "without breath"), and usually last 20 to 40 seconds. More than 28 million suffer from OSA in the US and its occurrence in the adult population is estimated to be 3-4% in women and 6-7% in males. People who suffer from weight gain, obesity, craniofacial syndromes (mostly genetic), repair of cleft palpate, Down's syndrome, small mandible etc. have a higher risk of developing obstructive sleep apnea than most individuals. Our invention is mainly intended to treat these conditions causing obstructive sleep apnea.

2. Central sleep apnea is due to a neurological condition as a result of a head injury, stroke, or various central nervous system disorder, or heart failure. Patients with central sleep apnea should avoid using sedatives, narcotics, and alcohol. Treating the primary etiology will in most cases eliminate the condition. Treatment for central sleep apnea syndrome includes the use of medications. They are medroxyprogesterone, acetazolamide, theophylline, and nicotine. Avoid central nervous system depressants such as sedatives and alcohol. Many patients suffering from central sleep apnea also have some degree of obstructive sleep apnea unfortunately the primary etiology may be terminal.

3. Mixed sleep apnea is due to physical oropharyngeal airflow obstruction associated with central (CNS) etiology. It is a rare condition that is the most dangerous form of sleep apnea. Therefore, it is the most difficult to treat. The present invention provides a treatment for this form of obstructive sleep apnea.

Symptoms of Obstructive Sleep Apnea are frequent cessation of breathing (apnea) during sleep. A sleeping spouse or companion notices repeated silences from your side of the bed with sudden awakenings to restart breathing with choking or gasping during sleep to get air. Loud snoring, awakening in a sweat during the night due to lack of oxygen with an increase of carbon dioxide build up in the blood, waking up restless in the morning after a night's sleep with or without headaches also takes place in these patients. Sore throat, dry mouth in the mornings, daytime sleepiness including falling asleep at improper times, when driving to work, at meeting and conferences with fatigue are also noticed. Mood changes like irritability, anxiety, depression, trouble concentrating, forgetfulness reduced and dwindling sex drive, unexplained weight gain, increased urination and/or nocturia, frequent heartburn, gastro-esophageal reflux disease (GERD), and heavy night sweats can occur in the patients with obstructive sleep apnea.

Studies by Lee et al, shown that the oxygen desaturation associated with sleep events were detected in all patients with OSA, but not in simple snorers. (Lee C H, Mo J H, Kim B J, Kong I G, Yoon I Y, Chung S, Kim J H, Kim J W, Arch Otolaryngol Head Neck Surg. Evaluation of soft palate changes using sleep video fluoroscopy in patients with obstructive sleep apnea. 2009 eb; 135(2):168-72). When awake, inspiratory efforts increased the length and angle of the soft palate (SP) in patients with OSA but not in simple snorers. Elongation and angulations were greatest during desaturation sleep events and least during awake (FIGS. 1, 3). In normal oxygenation events, changes in the soft palate (SP) were significantly larger in patients with OSA than in simple snorers (P<0.01 for SP length; P=0.03 for SP angle). These studies showed that the SP was considerably elongated and angulated in patients with OSA even when awake. Hence, the treatment of snoring is differentiated for the sake of treatment: 1. to prevent production of sound during sleep, 2. to treat the obstructive sleep apnea, which has serious health consequences. Our invention is intended for treatments of both conditions.

There are no effective FDA approved drug treatments for obstructive sleep apnea. Nevertheless, a clinical trial of the anti depressant mirtazapine (Brand name: Remeron, Avanza, Zispin) has shown promising results in the treatment of Obstructive Sleep Apnea, but it causes weight gain and sedation ("First Effective Drug for Sleep Disorder Identified". ScienceDaily.com. June 2003). It is a tetra cyclic antidepressant (TeCA) used primarily in the treatment of depression. The drug may treat as a hypnotic, antiemetic, appetite stimulant, and for the treatment of anxiety. Mirtazapine is not a SSRI reuptake inhibitor. It disinhibits dopamine and norepinephrine activity in various parts of the brain in the pleasure centers such as the ventral tegmental area (VTA) which causes a pronounced antidepressant and anxiolytics response due to the release of the neurotransmitters dopamine and norepinephrine. Beside its close analogues, mianserin and setiptiline, mirtazapine is one of the small number of noradrenergic and specific serotonergic antidepressants (NaSSAs) that can be tried on OSA.

Other drugs that are tried are serotonin uptake inhibitors (SSRI) such as fluoxetine, tryptophan, protriptyline, oral methylxanthine, and theophylline (chemically similar to caffeine), amphetamines stimulants, and anti-narcoleptic medications such as modafinil. A course of anti-inflammatory steroids such as prednisone (or another glucocorticoid drug) is given to reduce the lymphoid tissue of the naso-oropharyngeal air passages if enlargement of the lymphoid tissue is found when the allergic conditions are suspected.

A basic treatment for snoring and obstructive sleep apnea involves having the patient sleep in the prone position or on his/her side. This can be put to use by sewing an object into the back of the snorer's clothes. In an obese person, treatment includes weight loss. These patients avoid use of CNS depressing drugs, cigarettes, or alcohol prior to bedtime to prevent or reduce the loss of oropharyngeal muscle tone.

Nasal and oropharyngeal obstruction due to enlarged tonsils and adenoids treated or relived by surgical removal. Surgical repair of deviated nasal septum improves snoring. Snoring can be due to genetics with some being predisposed towards an anatomical narrowing across the nasal-oral-laryngeal-pharynx resulting in the reduced pharyngeal passageway caused by a lack of muscle tone. Other anatomical conditions contributing to the narrowing of the naso-oro-laryngopharyngeal passageway include choanal atresia, chrono polyp, nasal septal deviation, nasal and pharyngeal cysts, macroglossia, retrognathia, micrognathia and countless other etiologies. (Leung et al, "The ABZzzz's of Snoring", Post Graduate Medicine; Sep. 1, 1992).

Snoring and OSA might be aggravated by alcohol drinks or drugs (such as tranquilizers, hypnotic, sleeping pills, and antihistamines) taken prior to bedtime. Smoking is also held responsible for snoring. The cigarettes may irritate the mucus membranes of the upper airway and oropharynx causing swelling and increased mucus production. When snoring is caused by nasal allergy or an upper respiratory tract infection, these conditions can be treated with antiallergic treatment (Douglas N J. "The Sleep Apnoea/Hypopnoea Syndrome And Snoring", British Medical journal, 1993, Vol. 306:1057-60; Leung et al, IBID)

Anti-snoring and anti OSA devices abound in the medical device market. Some of them are shown to be effective when they pull or hold the mandible (lower jaw) forward and upward and elevate the tongue when the muscles of the mandible relax, so that the tongue does not occlude the air passageway drifting inferiorly and posteriorly while sleeping to prevent the passage of air (FIG. 1). Most anti-snoring devices accomplish this task by moving the lower jaw forward and holding that position against a rigid upper dental component fixed to the upper teeth in the immobile maxilla and to the moving lower teeth in the mandible. The disadvantages in using the above prior art devices are that they require expert qualified licensed lab services for fitting of the anti-snoring device to the user's mouth. Such devices could cause permanent irremediable changes in the bite of the user and permanently alter the jaw position. This requires a dentist to monitor the anti snoring device fitting. There is a need for an anti-snoring device that does not rigidly bind to the dental structures of the user's mouth and that does not require professional supervision or assistance in its fabrication, or monitoring of the dental bite changes and mandibular changes. In addition, the anti-snoring device should not pit the lower jaw against the upper jaw. These devices do not include an intra oral dental overlay to support the tongue against the palate and keep the palate of the user's mouth from reverberating (snoring) during mouth breathing. Our invention overcomes these drawbacks.

Snoring and obstructive sleep apnea can also be managed by the use of a positive pressure generator and facemask. In this procedure, a mask covers the nose and mouth or nose or mouth and delivers air under pressure. The standard method is known as "Continuous Positive Airway Pressure" (CPAP) treatment that requires the patient to wear a mask in which air is blown into the nostrils to keep the airway open. Patient compliance is poor due to discomfort and side effects. These machines pump air through a hose and nose/mouth facemask to keep air passages clear and open. CPAP pneumatically splints the upper airway. Use of the devices can cause the subject to become non-complaint due to difficulty in its use due to discomfort problems during sleep. Problems that may occur with CPAP include restless sleep, dryness of nose, throat, and nasopharyngeal tract, cough, excessive dreaming during early use, nasal congestion, runny nose, sneezing, irritation of the eyes and the skin on the face, abdominal bloating, and leaks around the mask when it does not fit properly.

The patient may be able to limit or stop some of the side effects. The doctor may be able to adjust your CPAP to reduce or eliminate problems to make sure the mask or nasal prongs fit you properly where air should not leak around the mask. The use of a humidifier, corticosteroid, nasal sprays to reduce nasal congestion, irritation, and drainage used if beneficial.

Users of this method of treatment may need to talk to a doctor about trying a CPAP machine that will help to reduce discomfort caused by too much constant pressure in the user's nose. If this does not improve discomfort, ask your physician about trying a bi-level positive airway pressure machine (BiPAP-VPAP or variable positive airway pressure), which uses a different air pressure when you breathe in when you exhale. BiPAP may work better than standard CPAP for treating obstructive sleep apnea in people who have heart failure. BiPAP machines are more expensive than CPAP machines.

When one is using CPAP or BiPAP, the person needs to see their doctor and sleep specialist regularly. There may be a need for more sleep studies to adjust the CPAP machine and check whether the treatment is working. The sleep studies and the CPAP machines are expensive. A patient can rent a CPAP machine before purchasing one. The most common problem with CPAP is lack of compliance. This means that people do not use the machine every night because the machine is uncomfortable. The patient may remove the machine as they sleep which leaves the patient sleepy the next day due to repeated interruption during sleep.

In 2008, a device with Nasal Expiratory Positive Airway Pressure (EPAP) increasing device named Provent™ was introduced by Ventus Medical. The provent device contains two pinhole-size valves, one over each nostril. The valves let air in easily—most people breathe through their nostrils while asleep—but there is resistance as the user exhales. That resistance creates a backpressure in the airways, dilating the muscles that would otherwise collapse in the middle of the night. In the morning, the patch removed; a new one used every night. This device is not effective in all cases. Some people do experience difficulty inhaling and exhaling air, and are uncomfortable due to the buildup of positive pressure during exhaling and take longer to fall asleep with the device on. The study by Berry et al. studies show that the nasal EPAP device improved subjective daytime sleepiness compared to the sham treatment in patients with OSA (Berry R B; Kryger M H; Massie C A. A novel nasal expiratory positive airway pressure (EPAP) device for the treatment of obstructive sleep apnea: a randomized controlled trial. SLEEP 2011; 34(4): 479-485). It is ineffective in severe form of obstructive sleep apnea.

A more recent treatment option to obstructive sleep apnea includes the implantation of rigid inserts in the soft palate to provide structural support. This is both invasive and only effective for mild to moderate cases of obstructive sleep apnea. Alternative treatments are even more invasive and drastic: including tracheostomy, genioglossus advancement or stimulator, hyoid suspension, tongue reposition, and tissue ablation (somnoplasty or uvulopalatopharyngoplasty (UPPP)).

If all else fails, sleep apnea can be treated by maxillomandibular advancement. It is a complex operation, in which the maxilla holding the upper teeth and the mandible holding the lower teeth are surgically cut, and the lower part of your face moved forward approximately 12 millimeters. In this complex surgical procedure, the airway in the back of the throat is expanded to relieve the obstructive sleep apnea. This undertaking is advised only for disabling obstructive sleep apnea patients in whom other treatments have failed. Other treatments include reduction of the size of the soft palate, laser-assisted uvulopalatoplasty, reduction of the tongue base either with laser excision or radiofrequency ablation, Genioglossus Advancement, Hyoid Suspension in which the hyoid bone in the neck are attempted to treat this condition. In rare intractable cases, tracheostomy is the only effective treatment for sleep apnea.

Due to many associated disadvantages, complications and high failure rate, these tissue ablation methods and radical surgeries considered as a last resort. Other options for treating snoring are found with surgical techniques where there are removal of enlarged adenoids, tonsils, and host of other therapies recommended. Surgical removal of the uvula, distal portion of the soft palate, the anterior tonsillar pillars, and the redundant lateral pharyngeal wall mucosa said to increase the size of the air passageway allowing unobstructed movement of air through the pharynx. Rates of success of the uvulopalatopharyngoplasty reported to be in a range from 15% to 65% (Douglas, "The Sleep Apnoea/Hypopnoea Syndrome And Snoring", British Medical journal, 1993, Vol. 306:1057-60). In some instances, surgical repair of a deviated nasal septum may improve snoring but not OSA.

Consequences of snoring and obstructive sleep apnea are exhaustion due to lack of sleep, interfering with work, and sleepiness while driving. Obstructive sleep apnea causes high blood pressure, depression, irregular heartbeats, heart failure, coronary artery disease, and stroke. If the person is overweight, bariatric surgery may help to lose weight and improve sleep apnea.

Snoring and obstructive sleep apnea patients with decreased pulmonary function such as emphysema, asthma, chronic obstructive lung diseases (COPD), and congestive heart failure are shown to suffer from severe apnea. Cessation of breathing during snoring, or obstructive sleep apnea results in lack of oxygen due to an obstructed nasopharyngeal passageway that deprives the body of sufficient oxygen with oxygen desaturation arises. Lack of oxygen may cause the brain to awaken the sleeper to take a breath without fully waking. This may happen dozens and even hundreds of times a night. The snorer and OSA patients do not get sufficient sleep. Being aroused from deep REM sleep on a repetitive basis increases heart rate and blood pressure with associated risks of heart attack and stroke. Furthermore, narcolepsy resulting from exhaustion can cause a lack of attention for the snorer and OSA sufferers during waking hours causing a drop in productivity and accident proneness at work, driving, and other daily activities.

Several attempts are made to treat OSA and snoring using many implants and devices placed in either the tissue of the soft palate or the pharyngeal airway as disclosed in U.S. Pat. No. 6,250,307; U.S. Pat. No. 6,523,542; and U.S. Pat. No. 6,431,174 and U.S. Pat. No. 6,601,584.

Another technique to treat OSA and snoring includes debulking tissue by applying radio frequency ablation to the tongue base or of the soft palate to debulk the tissue of the tongue or palate, respectively. This technique illustrated in U.S. Pat. No. 5,843,021 (Powell et al. "Radiofrequency tongue base reduction in sleep-disordered breathing: A pilot study", Otolaryngol. Head Neck Surg., Vol. 120, pp. 656-664 (1999). U.S. Pat. No. 6,161,541 for OSA include stimulation of the hypoglossal nerve (Eisle et al., "Direct Hypoglossal Nerve Stimulation in Obstructive Sleep Apnea", Arch. Otolaryngol. Head Neck Surg., Vol. 123, pp. 57-61 (1997)). There are methods described to place struts or magnet in the tongue (U.S. 2005/0199248 AD, U.S. 2004/0139975, U.S. 2004/0149290). U.S. Pat. No. 7,845,357 B2 describes Tongue Implant for Sleep Apnea. Many of these are invasive procedures, and patients are not willing to undergo these drastic procedures. Besides the expenses, the success rate is not guaranteed.

U.S. Pat. No. 5,569,679 discloses the use of nasal solution 10%-16% of methylsulfonylmethane (MSM) drops for the treatment of anti snoring method. This nasal spray is too simplistic to a complicated anatomically related snoring with or without obstructive sleep apnea whose pathophysiology is not in the nose.

U.S. Pat. No. 5,921,241 discloses an anti-snoring device including a moldable dental overlay for covering the lower teeth of the user and for maintaining the tongue in contact with the palate to prevent airflow from causing the palate to reverberate during mouth breathing.

U.S. Patent Application Publication Number: U.S. Patent Application Publication Number: 2004/0153127 A1 invention provides electrical stimulation that causes the oropharyngeal muscles to contract during sleep using one or more micro stimulators injected into or near these muscles or the nerves which innervate them.

U.S. Patent Application Publication Number: US 2007/0233276 A1 describes the method and apparatus include placing a tissue contractor within the tongue tissue. This is invasive procedure and may create discomfort and complication after surgery.

U.S. Pat. No. 6,418,933 B1 discloses an anti-snoring device has maxillary and mandibular bite forms with outwardly extending pivots which are mounted to the bite forms by frameworks which are at least partially embedded in the bite forms.

U.S. Pat. No. 5,499,633 shows two bite forms that may be joined so that the user's mandible projects forwardly of its normal position in order to reduce snoring.

U.S. Patent Application Publication Number: 2005/0178392 A1 discloses a small piece of cloth tape or other porous hypo allergenic material with a hypoallergenic adhesive on the back affixed to the lips before sleeping. This may not be effective in preventing the vibration of the soft palate and snoring with or without obstructive sleep apnea.

U.S. Pat. No. 7,016,736 B2 discloses a submental electrical stimulation of the supra hyoid muscles at the floor of the mouth, and does not address the snoring due to vibration of the soft palate and uvula.

Numerous management techniques have been described, and none of these treatments have proved adequate. Most of the therapies are inadequate to treat snoring and obstructive sleep apnea. Surgery for the condition is fraught with fear and complications besides high cost and high rate of failure. Hence, snoring and obstructive sleep apnea remains a serious health problem. With increasing obesity (Syndrome X), snoring with or without obstructive sleep apnea is increasing in the general population along with type II diabetes. Accordingly, there has been a need for improved management techniques to reduce or eliminate snoring and obstructive sleep apnea using simple and safe methods. The devices in the present inventions designed to treat snoring and obstructive sleep apnea with minimum or no complications, the least amount of disadvantage, and highest amount of user compliance with low cost.

SUMMARY OF THE INVENTION

The present invention is a safe, inexpensive, easy to use and effective anti-snoring and anti-sleep apnea treatment device. The device has a vertical and horizontal bar. The horizontal bar is placed inside the mouth, behind or between the molar teeth with palatine and tongue shelves to prevent snoring and movement of the tongue backwards. The device is tethered to the hard palate by vacuum cups to prevent the movement of the tongue backwards during sleep to prevent sleep apnea. The proximal end of the vertical bar is anchored to string at the distal end with hook and loop fabric closure adhesive attachment and to the lips outside the mouth to prevent the accidental swallowing and aspiration of the device; and at the same time holds the tongue and device firmly in the mouth. The device is provided with canula with three way stopcocks to deliver supplemental oxygen and therapeutic agents.

One object of the present invention is to provide a new, useful, simple, and effective device for the prevention and treatment of snoring and obstructive sleep apnea (OSA).

Another object of the present invention is to provide a safe and effective treatment device that can be self fitted or inserted in the mouth by a snorer and/or obstructive sleep apnea patient before going to sleep.

A further object of the present invention is to provide a safe and effective treatment device inexpensively to prevent snoring and obstructive sleep apnea.

An important function of this invention is to allow unobstructed movement of the air through the nose, mouth, and pharynx to the larynx to prevent hypoxia, snoring, and obstructive sleep apnea.

The present invention is to provide an inexpensive method to reduce the incidence of snoring and obstructive sleep apnea that is safe and effective.

The goal of the present invention is to provide an invention that relates to a device inserted into oral cavity behind the molar teeth (or on the molar teeth dental cap if reto-molar space is not accessible), which has palate and tongue shelves that extend all the way to the posterior aspect of the tongue, to prevent snoring and obstructive sleep apnea.

The goal of the present invention is where the device is in contact of the base of the tongue and the soft palate, to prevent flaccid tissue closing of the oropharyngeal air way that cause snoring and OSA during sleep.

The device described in this invention comes in contact if the tongue and soft palate becomes flaccid and falls back during sleep to cause snoring and OSA.

The apparatus placed on the dorsal surface of the tongue in the middle held by horizontal bar placed behind the molar teeth. It can be bent to adjust to the convexity of the tongue upper surface and height of the palate splint—shelf and can be adjusted for comfort.

The body of the apparatus is made as one piece of plastic material, malleable metal, or silicone and other combinations of synthetic or semi synthetic composite material.

The shape of the apparatus conforms to the shape of the top part of the tongue, slightly convex upwards to be able to place it easily so that it fits snugly.

The convex surface of the apparatus is a convex metal shelf splint or projection (palate shelf splint) splint that prevents the soft palate coming down and being in touch with the tongue to produce the sound of snoring associated with or without obstructive sleep apnea.

This novel apparatus has a quadrangular, or round metal, plastic plate or metal shelf splint (square ring projection) which is concave in shape to fit in the posterior part of the tongue, and prevent the moving of the tongue backwards and does not occlude the air passageway drifting inferiorly and posteriorly while sleeping. This tongue shelf splint prevents the passage of air by coming in contact with the pharyngeal wall that produces snoring and obstructive sleep apnea.

Another object of the present invention is to provide a safe and effective treatment device, which can be self, fitted, or inserted in the mouth by a snorer and obstructive sleep apnea patients before going to sleep.

A further object of the present invention is to provide a safe and effective treatment device inexpensively to prevent snoring and obstructive sleep apnea device with a lower jaw extending bite block incorporated.

An important function of this invention is in allowing unobstructed movement of the air through the nose, mouth, and pharynx to the larynx to prevent hypoxia, snoring, and obstructive sleep apnea.

The device has two "V" angle shaped incisor teeth receivers made of metal or synthetic plastic to fit the upper and lower incisor teeth (incisor teeth receptacles) which can be adjusted to the comfortable levels to pull the lower jaw on the fixed upper jaw to prevent the movement of the tongue backwards resulting in snoring and OSA.

The device can be provided with an oxygen canula to supply oxygen from the oxygen tank or oxygen generator to provide supplementary oxygen to the laryngeal inlet for those who are pulmonary function compromised.

The device can be provided with an injection port and canula to deliver any therapeutic agents and local anesthetics to reduce the sensitivity of the oropharyngeal passages when the device is placed in the mouth before sleeping. The same injection port used to deliver therapeutic agents to the surface of the tongue and palate can be used to treat halitosis and other disease afflictions of the oral cavity.

The invention device is made up of hypo-allergic, non-toxic, and non-reacting synthetic, natural biodegradable or combinations composite material with metal and silicone.

BRIEF DESCRIPTION OF THE DRAWINGS

The present invention is to be understood with reference to the following drawings. The embodiments of the apparatus or device components in the drawings are not necessarily to scale, stress instead being placed upon visibly, and clearly illustrating the principles of the present invention. In the drawings, like reference numerals designate corresponding parts throughout the numerous views of the figures. The purpose of the present invention will become readily clear and implicit from deliberation of the following comprehensive descriptions of the preferred embodiments when taken together with the accompanying drawings, in which.

DETAILED DESCRIPTION OF THE INVENTION

According to a present invention, the snoring and the obstructive sleep apnea (OSA) patients are treated by recognizing the condition is attributable in part to due to the vibration of the soft palate during inspiration (snoring) and movement of a base of the tongue of said patient toward a pharyngeal wall of the patient, which causes obstructive sleep apnea. The method includes detecting a region in the tongue extending from the mandible to the base of the tongue, preventing the muscular tissue of the tongue moving back towards the pharynx, and vibration of the soft palate resulting in the snoring and obstructive sleep apnea. The present invention prevents the tongue of the patient from obstructing the air passage that causes OSA. The proximal portion of the device is secured to the teeth by use of Incisors teeth receptacles, and lip anchoring string with adhesive. This invention holds the soft palate and tongue in such a position by Palatine and tongue shelf splint that they do not allow palate to vibrate and the tongue does not move back to cause OSA.

We will now reference the various figures in which identical embodiments numbered alike throughout the description of the preferred device of the present invention, presented at this time.

Figure 1:
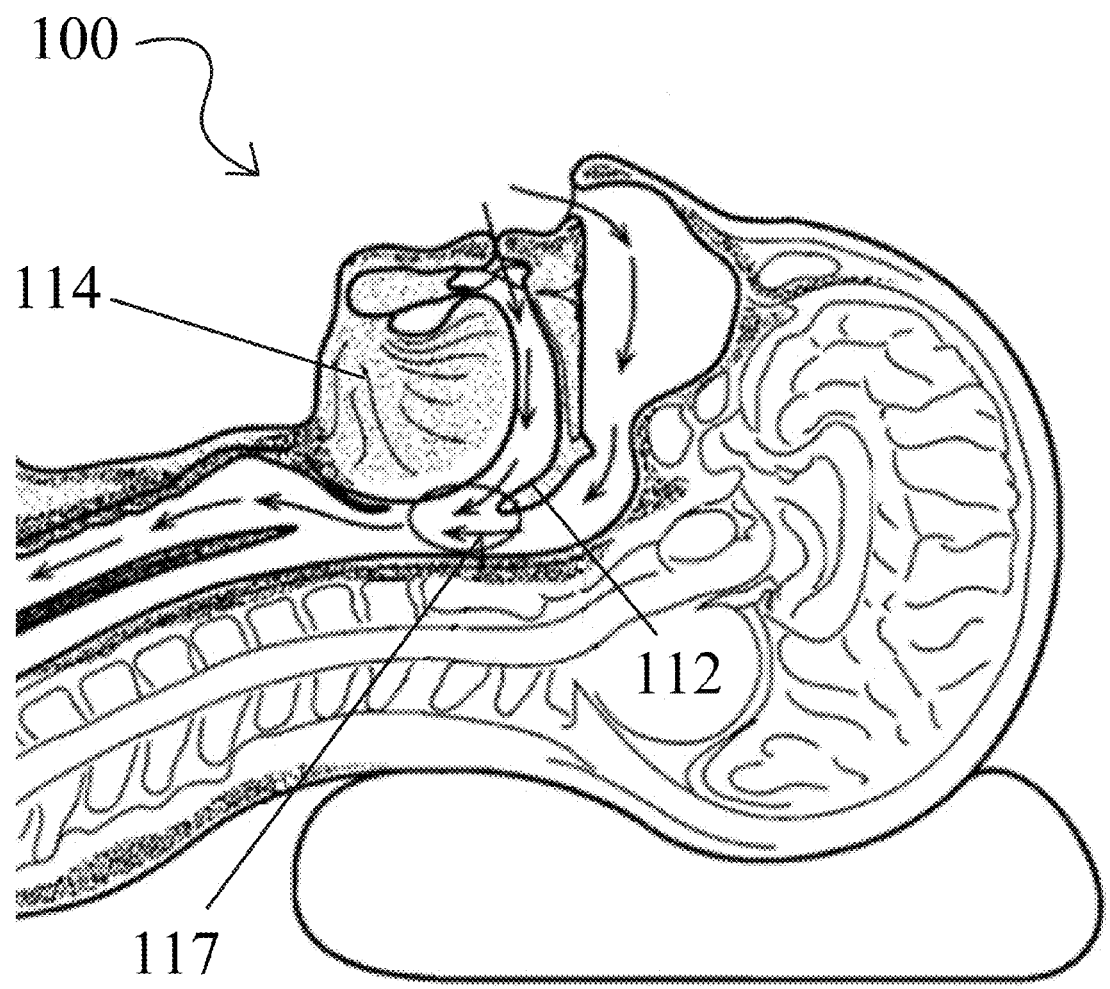
FIG. 1 is the diagrammatic presentation 100 of the airway during awake and sleeping.

FIG. 1 is the diagrammatic presentation of the normal airway 100 with the soft palate 112 and tongue 114 not obstructing the airway passage 117 allowing the free flow of air from the mouth and the nose to larynx as the person sleeps on a pillow in supine position. The airflow does not produce a physical force like a narrow air stream; hence, neither snoring, nor obstructive sleep apnea is produced.

Figure 2:
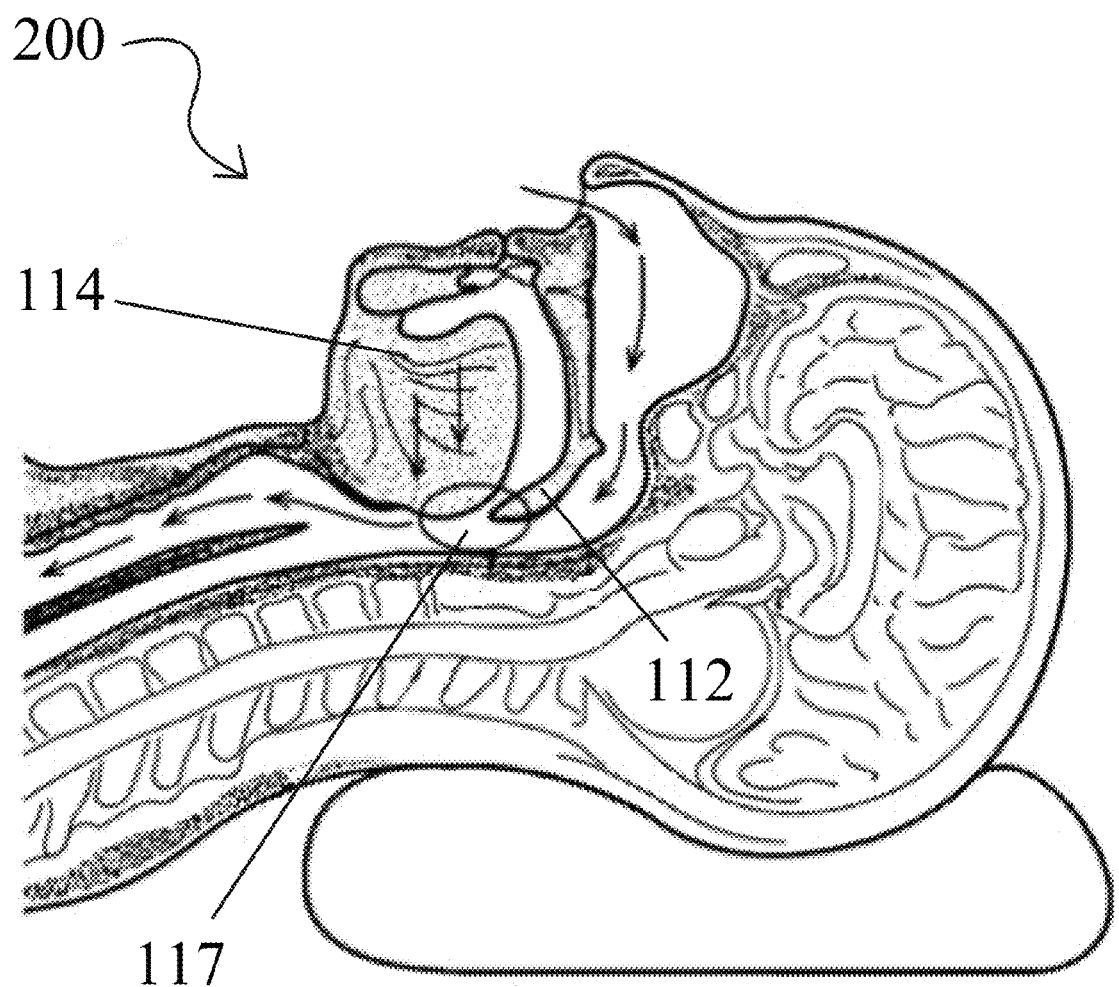
FIG. 2 is the diagrammatic presentation of the airway 200 with soft palate 112 and tongue 114 partially obstructing the airway resulting in snoring.

FIG. 2 is the diagrammatic presentation of the airway 200 with the soft palate 112 and tongue 114 partially obstructing the airway 117 not allowing the free flow of air from the mouth and the nose as the person sleeps. The air flows in a narrow stream through the air passages 117 vibrating the soft palate 112 and soft tissue around the tongue 114 producing snoring as one sleeps. This is due to relaxation of the soft palate 112 and tongue 114 becoming flaccid and falling back to create forcible air stream like a venturi wind tunnel effect, especially the soft palate 112, which does come in contact with narrow stream force of air close to the oropharynx to produce sound as one falls asleep. Our invention prevents the soft palate and tongue coming in contact and thus prevents snoring and sleep apnea.

Figure 3:
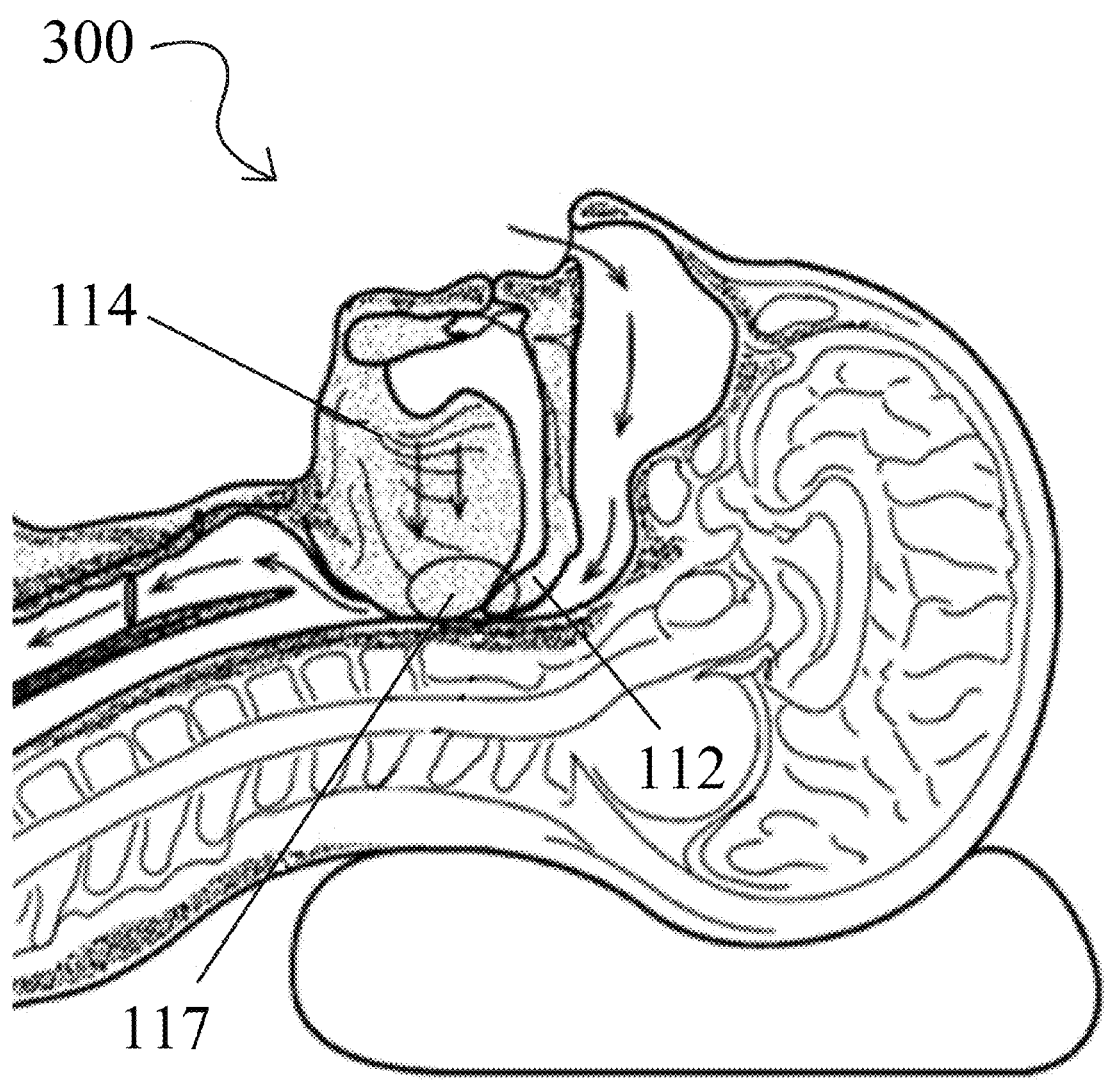
FIG. 3 is the diagrammatic presentation of the airway 300 with soft palate 112 and tongue 114 completely obstructing the airway resulting in obstructive sleeping apnea (OSA).

FIG. 3 is the diagrammatic presentation of the airway 300 with the soft palate 112, and tongue 114 completely obstructing the airway 117 by not allowing the free flow of air from the mouth, and the nose to the larynx, through the oropharyngeal air passageway to the laryngeal inlet as a person sleeps. This is due to relaxation of the soft palate 112 and the tongue 114 becoming flaccid and falling back due to reduced skeletal muscle tone on the wall of the oropharynx 117 creating obstruction to passage of air resulting in snoring and obstructive sleep apnea. Due to this physical blockage by the tongue, the sleeper becomes aware of the obstruction due to central nervous system activation by carbon dioxide build up in the blood due to lack of ventilation. This result in the partial opening of the airway allowing the air stream which causes the vibration of the soft tissue of the oropharynx, especially the soft palate 112, which comes in contact with narrow stream force of air so as to produce snoring sound as one falls asleep. The narrow stream of air flow or complete obstruction to air passage 117 results in vibrating the soft palate 112, and the soft tissue around the tongue 114 producing snoring and complete obstructive sleep apnea (OSA). Our invention prevents such a movement of the palate and tongue to cause obstructive sleep apnea, and allows the air to pass to the larynx.

Figure 4:
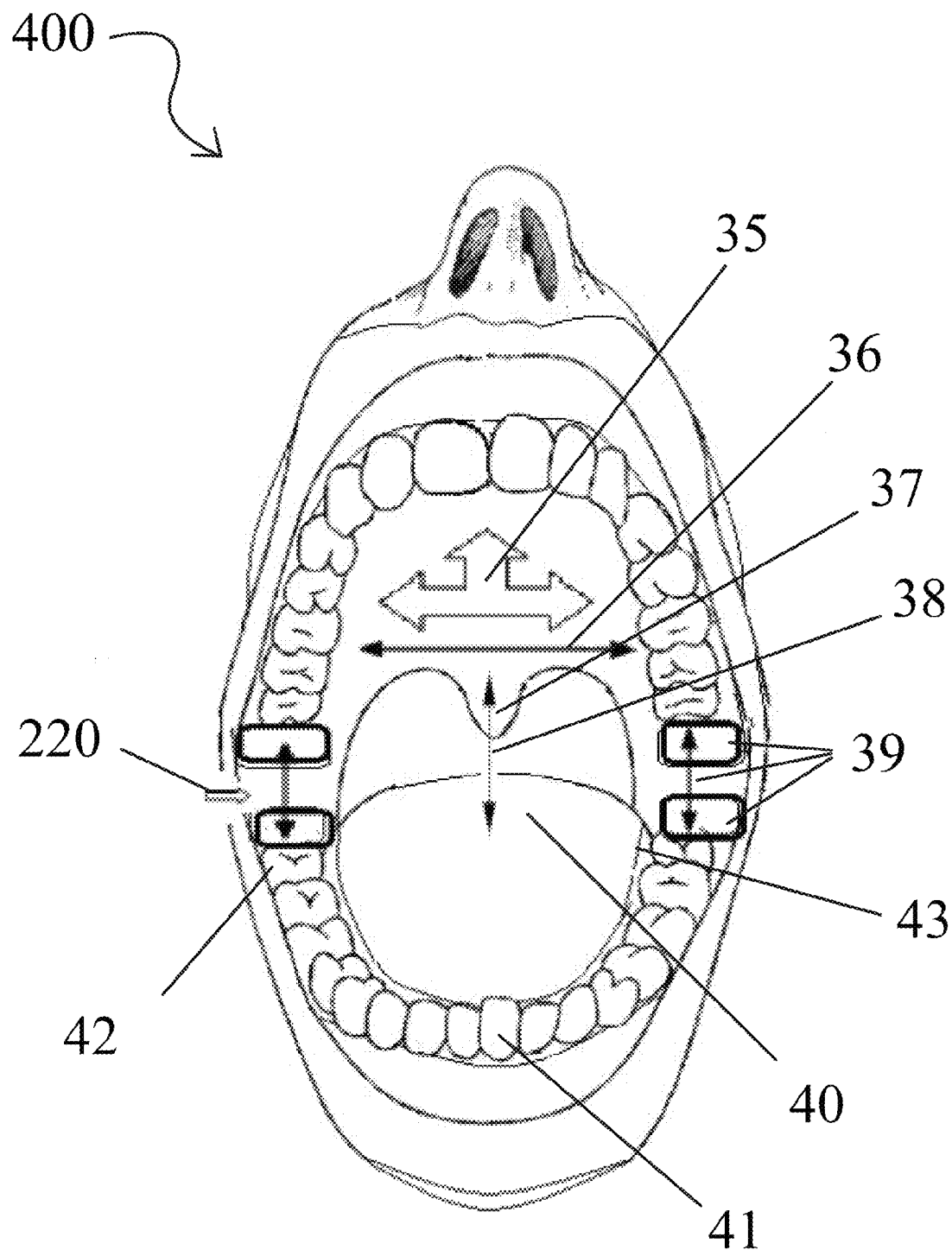
FIG. 4 is the view of the diagram 400 showing the mouth open with various anatomical regions of the mouth, teeth, and the tongue, on which the present inventive device 220 is placed to prevent snoring and obstructive sleep apnea.

FIG. 4 is the view of the diagram 400 showing the mouth open with various anatomical regions of the mouth, teeth, and the tongue, on which the present inventive device 220 is placed to prevent snoring and obstructive sleep apnea. This is the view of the fully opened mouth showing hard palate 35, Soft palate 36, Uvula 37, opening between the uvula and the tongue 38, allows the air and food to pass through the mouth. It is the narrowing of this space 38 with falling back of the tongue 40 which is responsible for snoring and obstructive sleep apnea. The dorsum of the tongue is immediately below the uvula. Note the space 39 between the upper and lower molar teeth 42. This presents an opening to place a device in this space to prevent the uvula and dorsum of the tongue coming in contact and moving posteriorly and inferiorly to cause snoring and obstructive sleep apnea. Back of the molar teeth with molar negative mould also presents an opportunity to place this device 220 close to the location involved in the snoring and obstructive sleep apnea. Commencement of the soft palate is in line with the line drawn between the retro molar teeth 39, which presents an ideal site to place the present inventive device. Thus, it prevents the soft palate meeting the dorsum of the tongue and backward movement of the tongue. That is the function of this inventive device 220 illustrated in FIGS. 6-20, to act as an anti-snoring and anti-obstructive sleep apnea device.

Figure 5:
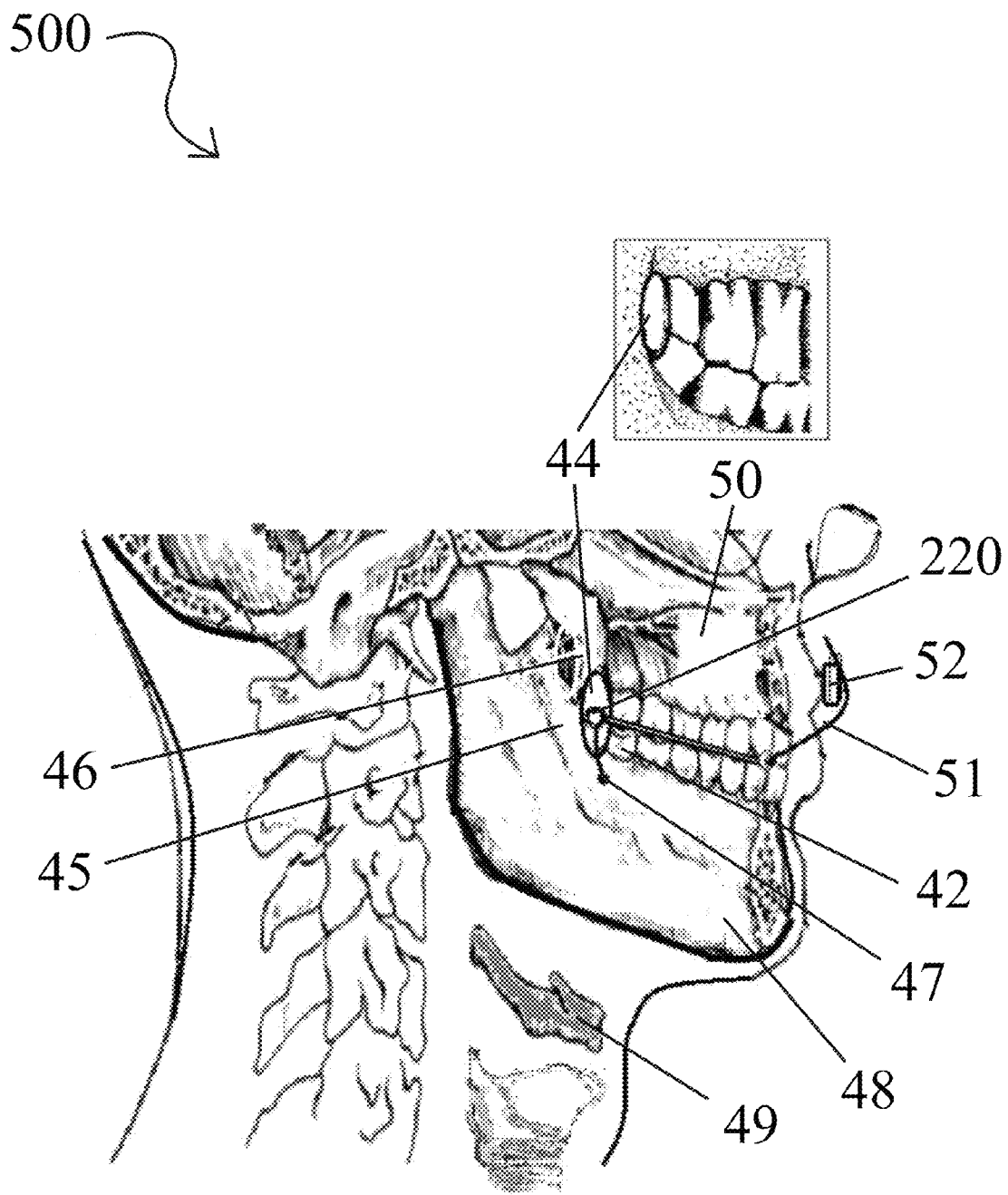
FIG. 5 is the side view of the skeletal diagram 500 of the jawbones 48, 50, and the hyoid bone 49, showing the location of the device 220.

FIG. 5 is the lateral view of the skeletal diagram 500 of the jaw bones 48, 50, the hyoid bone 49, above the thyroid cartilage, showing the location of the device 220 used for stopping snoring and obstructive sleep apnea, placed in the mouth between the upper and lower retro-molar space 44 behind the (1, 2) $3^{rd}$ molar teeth. It shows the post molar space 44 situated in front of the ramus 45 of the mandible 48 and below the pterygoid processes 46 above, bound in front by third molar teeth 42 located between the mandible 48 and maxilla 50. The horizontal ends 54 of the device 220 (see FIGS. 6, 7, and 8) are placed in these spaces 44 on both sides of the jaw. The vertical extensions 47 and 77 (see FIGS. 6-20 #47) from the ends of the horizontal bar of the device 220 hold the device in position firmly in place with hardly any movement. Note the anchoring string 51 from the vertical bar of the device with hook and loop fabric closure 52 attached to the lips, which prevents the moving of the device backwards or accidentally swallowed or aspirated.

Figure 6:
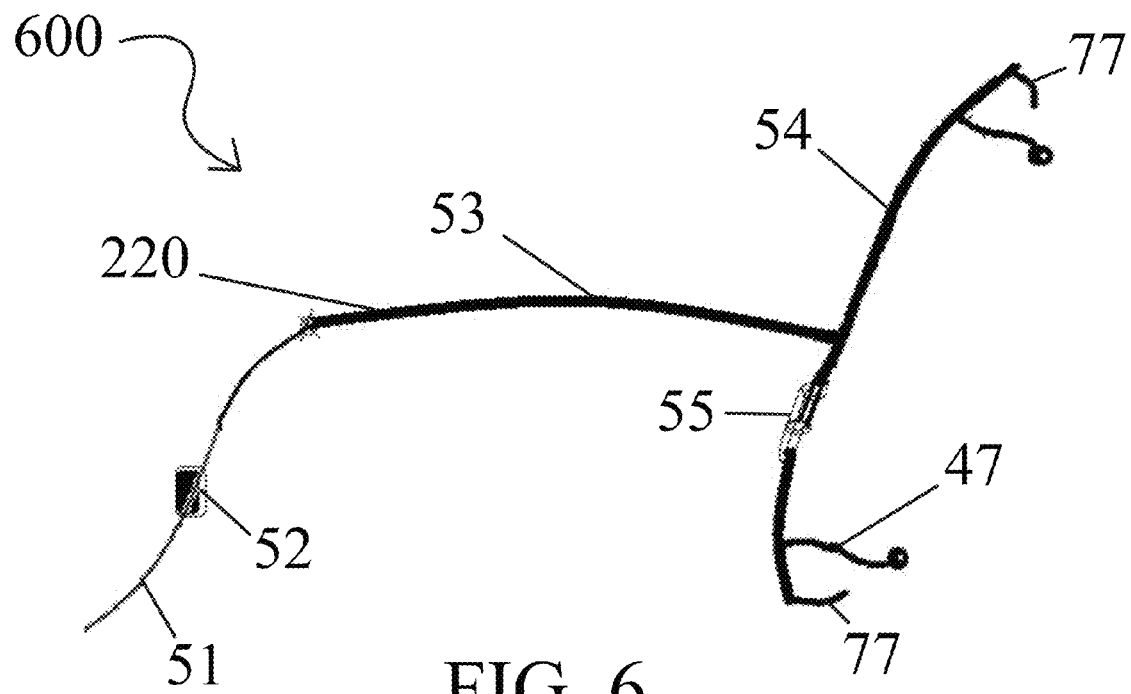
FIG. 6 is the view of the diagram 600 showing the device 220 placed in the mouth in the retro-molar space.

FIG. 6 is the simple view of the diagram 600 showing the device 220 placed in the mouth in the retro-molar space or on the last molar teeth as described above as anti-snoring and anti-obstructive sleep apnea device. As we go further, other embodiments added to the basic frame, to make this device 220 more effective. It has horizontal bar 54 attached to vertical bar 53. The vertical and horizontal bars are slightly concave to fit the convex dorsal surface of the tongue snugly. At the junction of the vertical and horizontal bar, it is further modified as described in FIG. 7 onwards to hold the soft palate and tongue in place. The horizontal bar in the mouth will function for light snorers and obstructive sleep apnea, but not in those who snore heavily and have a severe degree of obstructive sleep apnea, for which additional embodiments designed and added as described below. The horizontal bar has the telescoping embodiment 55 so that the horizontal bar can be fixed snugly between the molars to fit the anatomical distance between molar teeth, which can vary from person to person. Our experience in testing this device to treat anti-snoring and anti-obstructive sleep apnea device showed us that it is easy to place this device behind the third molar maxillary teeth and close the jaws to hold between the two jawbones. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders. The anchoring string 51 with hook and loop (Velcro®) fabric closure 52, attached to the proximal end of the vertical bar 53 is affixed to the lips, and prevents the moving of the device backwards or accidentally swallowed or aspirated.

Figures 7A, 7B:
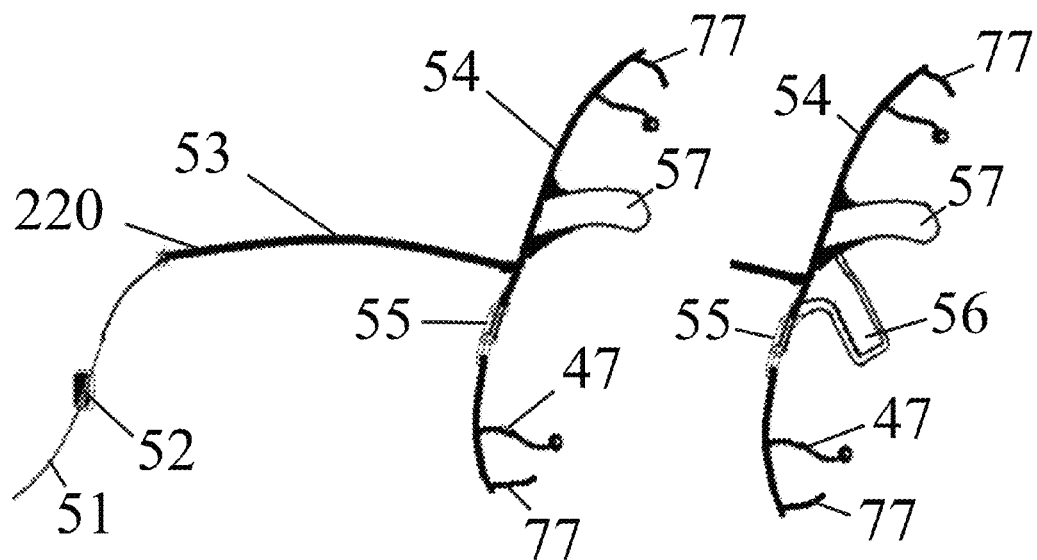
FIG. 7 is the view of the diagram 700 showing the device 220 placed in the mouth in the retro-molar space as described above as anti-snoring and anti-obstructive sleep apnea device.

FIG. 7, which has 7a and 7b, is the view of the diagram 700 showing the device 220 for placing in the mouth at the retro-molar space as described above as an anti-snoring and anti-obstructive sleep apnea device. It has the horizontal bar 54 attached to vertical bar 53. The vertical and horizontal bars are slightly concave to fit the convex dorsal surface of the tongue snugly. At the junction of the vertical and horizontal bar, there are two metal or plastic somewhat rigid extensions (shelves) 56 for the palate (FIG. 7a), 57 (FIG. 7b) for the tongue. The device 7a can be used exclusively for snoring, and in mild obstructive sleep apnea cases and device 7b used as both anti-snoring and anti-obstructive sleep apnea device.

These palatine and tongue shelves are made up of thin plates of metal, plastic, composite material or thick wires in an oblong shape. The extension shelf 57 holds the soft palate and the uvula upwards, whereas the extension projection 56 hold the tongue forwards, and prevents it sliding posteriorly and inferiorly during sleep. Such a move can result in obstructive sleep apnea and snoring. The horizontal bar has the telescoping embodiment 55 so that the horizontal bar is fitted snugly between the molars to fit the anatomical distance between molar teeth, which can vary from person to person. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders. The anchoring string 51 with hook and loop (Velcro®) fabric closure 52, is attached to the proximal end of the vertical bar 53 and is affixed to the lips, which prevents the moving of the device backwards or being accidentally swallowed or aspirated. Device 7a is used for an anti-snoring and device 7b is used as an anti-snoring and anti-obstructive sleep apnea device.

Figure 8:
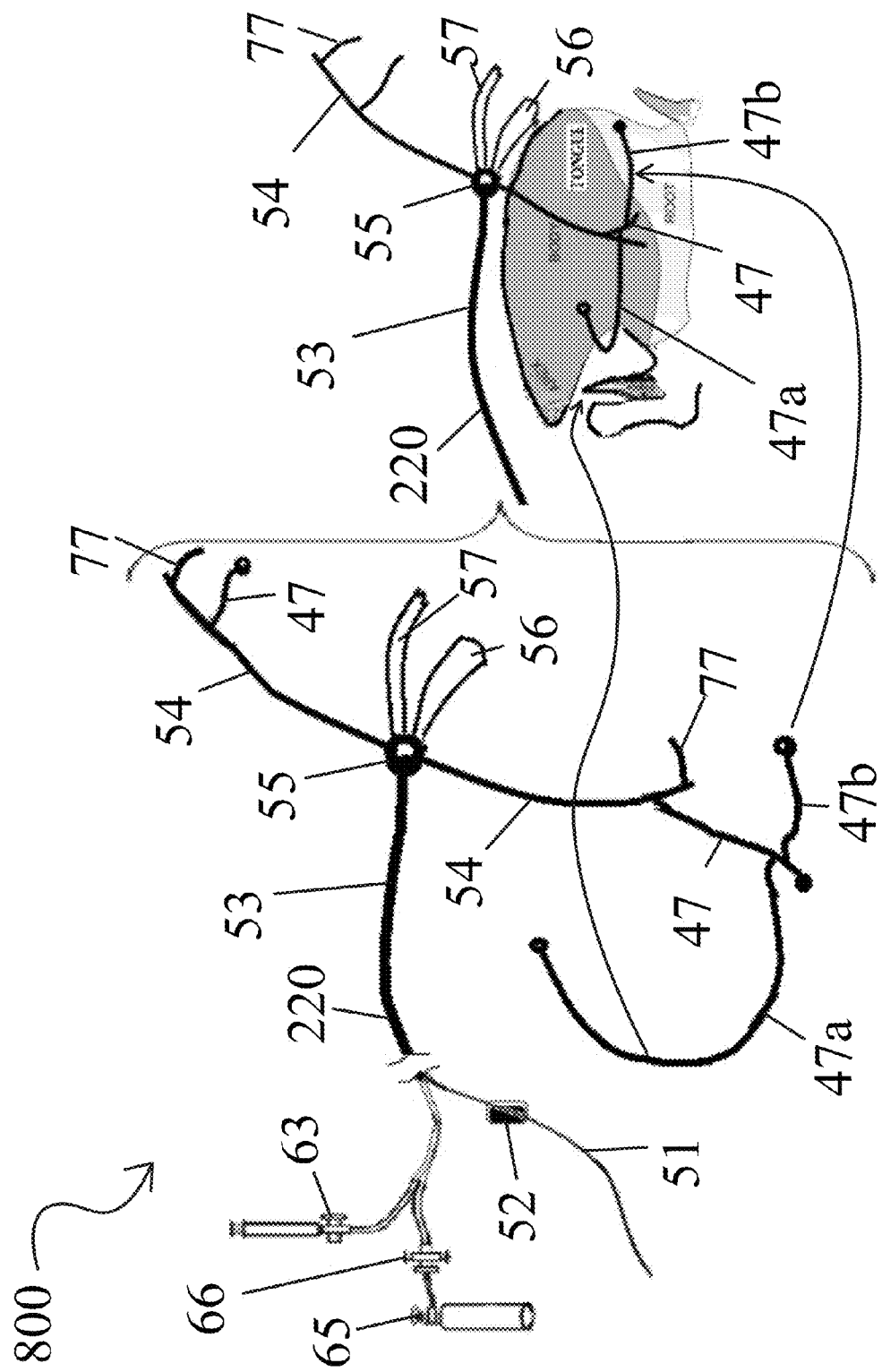
FIG. 8 is the view of the diagram 800 showing one of the embodiments used for stopping snoring and obstructive sleep apnea device 220 embodiments around the root of the tongue (800a).

FIG. 8 is the view of the diagram 800 showing one of the embodiments used for the stop snoring and obstructive sleep apnea device 220 placed in the mouth in the retro-molar space as described in FIGS. 4, 5. It has the horizontal bar 54 attached to the vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, whereas the extension projection 56 hold the tongue forwards, and prevents it sliding posteriorly and inferiorly. Such a move can result in obstructive sleep apnea and snoring. The horizontal bar has telescoping embodiment 55 so that the horizontal bar is fitted snugly between the molars to fit the anatomical distance between molar teeth, which can vary from person to person. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

Figure 20:
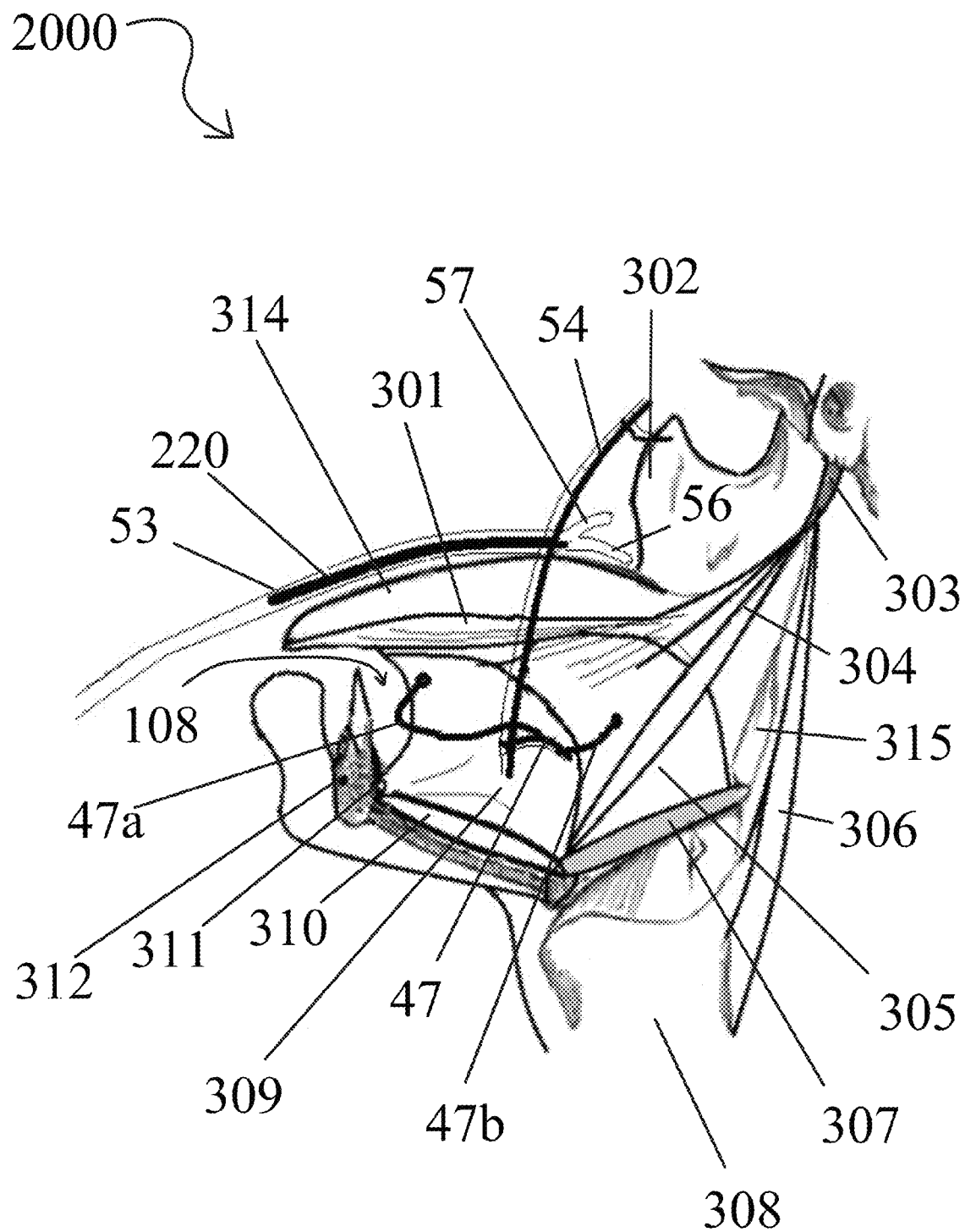
FIG. 20 is the diagrammatic presentation 2000 showing the muscles involved in the movement of the tongue and obstructive sleep apnea and how the presented inventive device prevents it.

From the end of the vertical extension (peg like) 47, two curved round rigid preformed plastic or metal wires 47a and 47b are attached, called tongue root holders. They hold the device 220 in position, and at the same time prevent the movement of the tongue backwards during sleep, which is the root cause of the obstructive sleep apnea. The 800a diagram incorporates the tongue to show how these tongue root holders or restrainers encircle the root of the tongue, thus hold back, hold down, pin down, confine, and prevent it moving backwards. Further, they also anchor the tongue between the device's vertical and horizontal bars 53, 54. The tongue root holders 47a, 47b prevent any movement of the flaccid tongue during sleep due to the relaxation of tongue muscles as shown in FIG. 20. The tongue root holders can be attached to the other end of the device as shown in the diagram 12 in full circle, or can be partial as shown in this FIG. 8 likened to a shape of a sickle.

The anchoring string 51 with hook and loop fabric closure 52 (VELCRO®) is also provided with this device, and it attaches to the proximal end of the vertical bar 53, and is affixed to the lips by hook and loop fabric closure adhesive 52, and prevents the moving of the device backwards or accidentally swallowed or aspirated. It also holds gives additional support to prevent the movement of the tongue backwards during sleep and thus prevent obstructive sleep apnea and snoring.

The device 220 can be provided with tubing and connections for supplemental oxygen delivery system 65, 66 that delivers oxygen at the laryngeal inlet at the back of the tongue. It can also have therapeutic agent's delivery tubing with a three-way stopcock and syringe 63 to deliver any therapeutic agents on the middle of the dorsal surface of the tongue to treat pathologic conditions of the tongue and oral cavity. This tubing can also deliver anti-halitosis therapeutic agents or local anesthetics to prevent bad breath and to reduce the sensitivity of the tongue.

Figure 9:
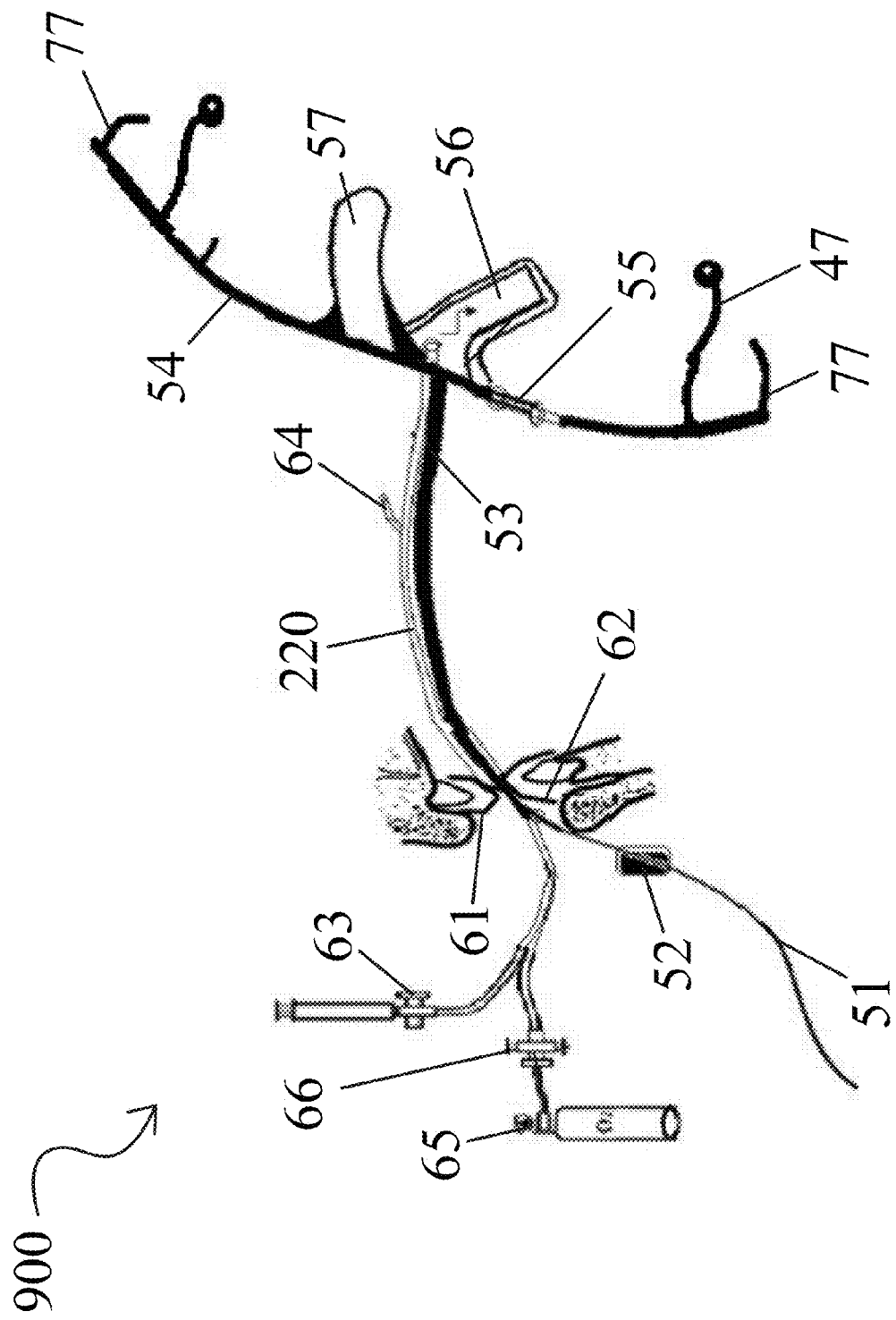
FIG. 9 is the view of the diagram 900 showing one of the embodiments used for stopping snoring and obstructive sleep apnea device 220.

FIG. 9 is the view of the diagram 900 showing the device 220 placed in the mouth in the retro-molar space as described above as an anti-snoring and anti-obstructive sleep apnea device. It has horizontal bar 54 attached to vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, where as the extension projection 56 hold the tongue forwards, and prevents it sliding posteriorly and inferiorly. Such a move can result in obstructive sleep apnea and snoring. The horizontal bar has telescoping embodiment 55 so that the horizontal bar fitted snugly between the molars to fit the anatomical distance between molar teeth, which can vary from person to person. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders. The anchoring string 51 with hook and loop fabric closure 52, is attached to the proximal end of the vertical bar 53 and is affixed to the lips, which prevents the moving of the device backwards or being accidentally swallowed or aspirated.

This device 220 incorporates V shaped incisor sockets 61, 62, at the proximal end of the vertical bar 53 to hold the device in position and prevent its movement backwards between the teeth. They also prevent the movement of the lower jaw against the fixed upper jaw backwards during sleep to prevent obstructive sleep apnea.

The device 220 can also be provided with tubing and connections for supplemental oxygen delivery system 65, 66 that delivers oxygen at the laryngeal inlet 59 at the back of the tongue. It can also have therapeutic agent's delivery tubing with a three-way stopcock and syringe 63 to deliver any therapeutic agents on the middle of the dorsal surface of the tongue 64 to treat pathologic conditions of the tongue and oral cavity. This tubing also delivers anti-halitosis therapeutic agents or local anesthetics to prevent bad breath and to reduce the sensitivity of the tongue.

Figure 10:
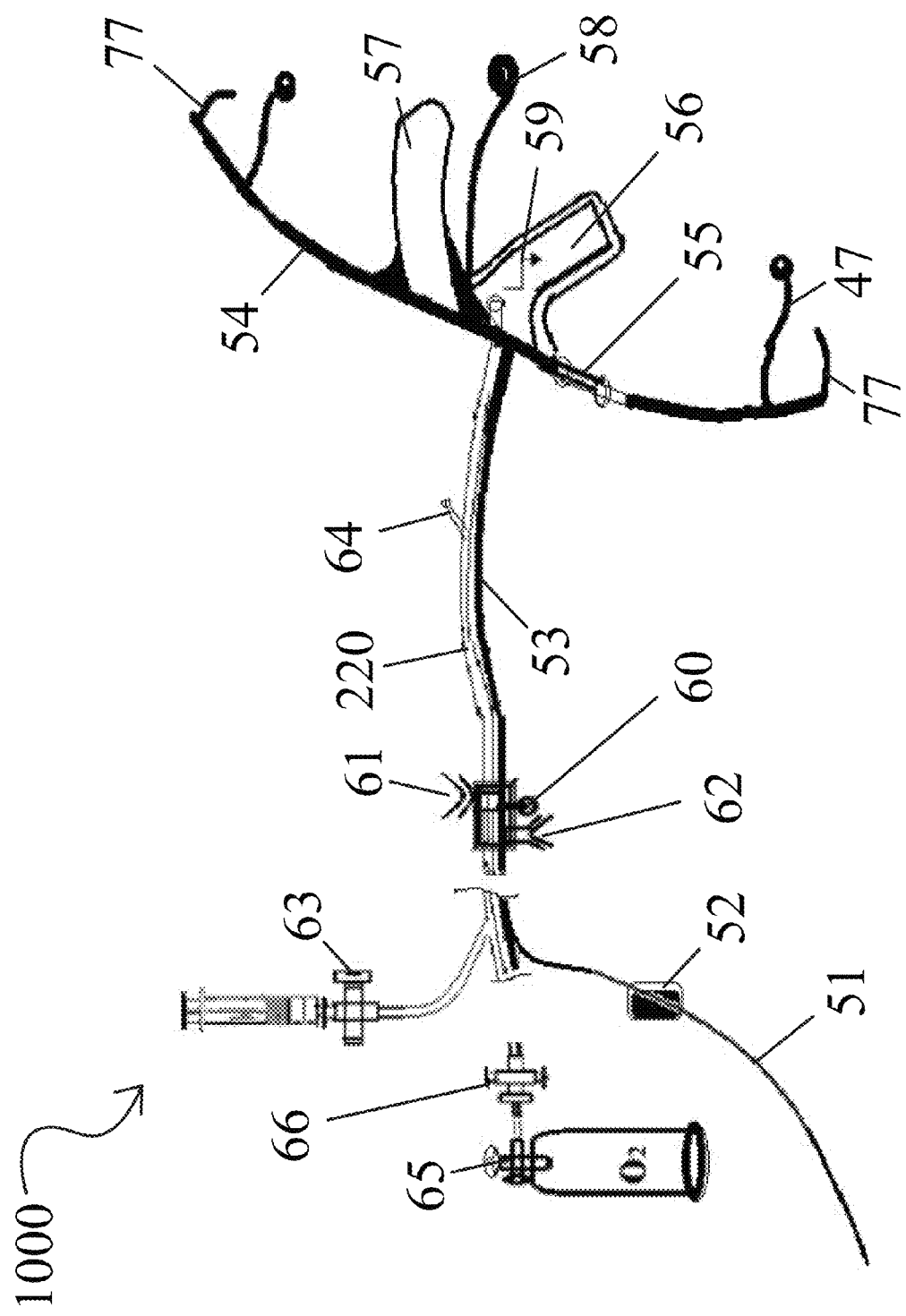
FIG. 10 is the view of the diagram 1000 showing one of the embodiments used for stopping snoring and obstructive sleep apnea device 220.

FIG. 10 is the view of the diagram 1000 showing the device 220 placed in the mouth in the retro-molar space as described above as an anti-snoring and anti-obstructive sleep apnea device. It has horizontal bar 54 attached to vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, whereas the extension projection 56 holds the tongue forwards, and prevents it sliding posteriorly and inferiorly. Such a move can result in obstructive sleep apnea and snoring. The horizontal bar has telescoping embodiment 55 so that the horizontal bar is fitted snugly between the molars to fit the anatomical distance between molar teeth, which can vary from person to person. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure 52, is attached to the proximal end of the vertical bar 53 and is affixed to the lips, which prevents the moving of the device backwards or accidentally swallowed or aspirated.

The device 220 also provided with tubing and connections for supplemental oxygen delivery system 65, 66 that delivers oxygen at the laryngeal inlet 59 at the back of the tongue. It can also have therapeutic agent's delivery tubing with a three-way stopcock and syringe 63 to deliver any therapeutic agents on the middle of the dorsal surface of the tongue 64 to treat pathologic conditions of the tongue and oral cavity. This tubing also delivers anti-halitosis therapeutic agents or local anesthetics to prevent bad breath and to reduce the sensitivity of the tongue if needed.

In addition, this device 220 incorporates V shaped incisor sockets 61, 62, at the proximal end of the vertical bar 53 to hold the device in position between the incisor teeth and prevent its movement backwards between the teeth. They also prevent the movement of the mobile lower jaw backwards on fixed upper jaw. These sockets are movable on the vertical bar 53 so as to move the lower jaw forwards on fixed upper jaw and has tightening screw 60 to hold the incisors sockets firmly in position during use after adjusting for the convenient location of the jaw forwards.

The device 220 also has a round small plastic or metal ball 58 attached to the center of the horizontal bar, with an extension bar which projects further than the embodiment 57 and 56 shelves. The function of this embodiment is to prevent the sliding of the tongue and the device backwards to encounter the pharyngeal wall and cause obstructive sleep apnea. It is an added safety mechanism for use in the severely affected obese snorers and obstructive sleep apnea sufferers.

Figure 11:
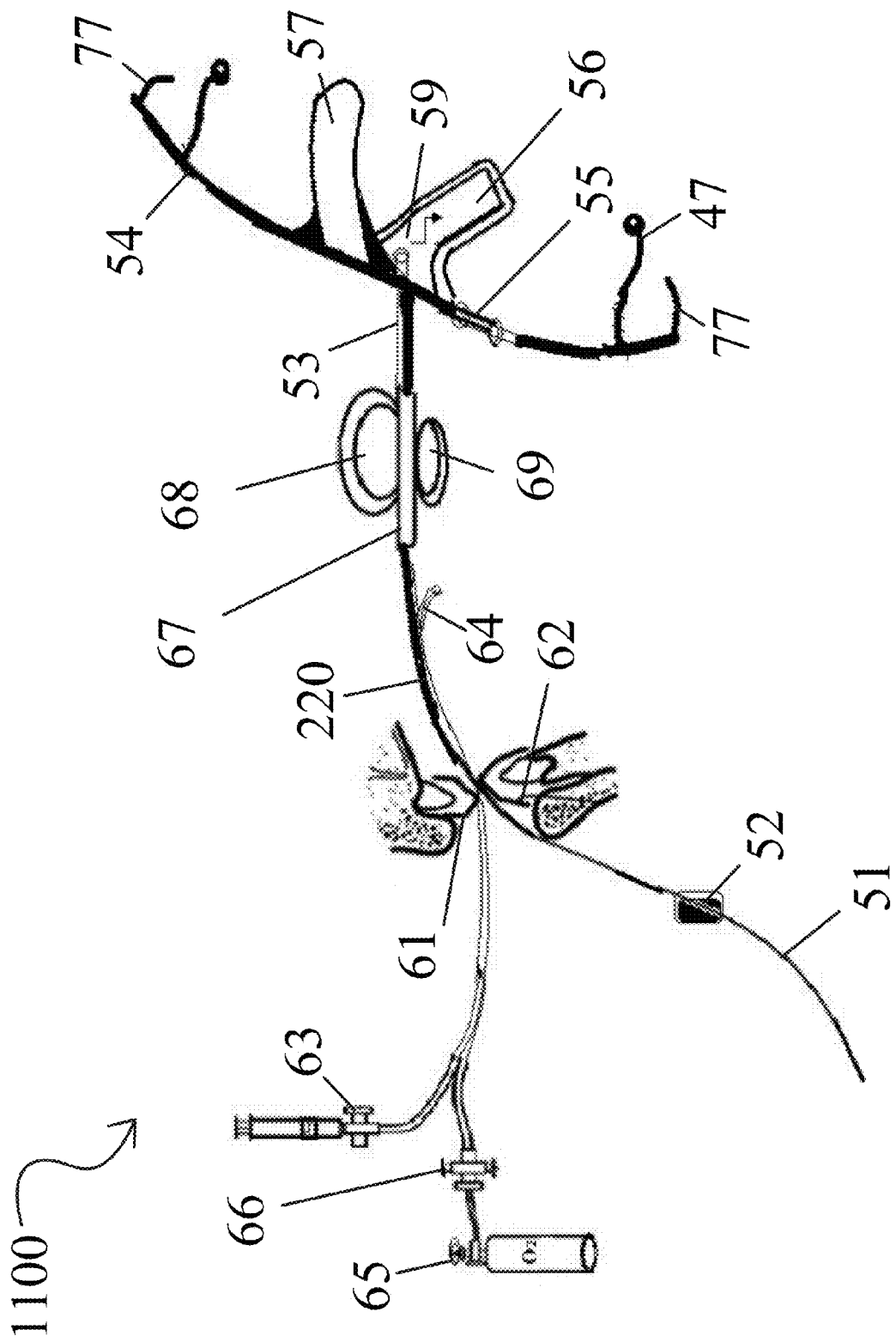
FIG. 11 is the view of the diagram 1100 showing one of the embodiments used for stopping snoring and obstructive sleep apnea device 220.

FIG. 11 is the view of the diagram 1100 showing additional embodiments of the device used for stopping snoring and obstructive sleep apnea device 220 placed in the mouth in the retro-molar space as described above. It has horizontal bar 56 attached to vertical bar 53. The vertical and horizontal bars are slightly concave to fit the convex dorsal surface of the tongue snugly. At the junction of the vertical and horizontal bar, there are two metal or plastic extensions 56, 57 made up of plates of metal, plastic, composite material or thick wires in an oblong square. The extension 57 holds the soft palate and the uvula upwards, whereas the extension 56 hold the tongue forwards, and prevents it sliding posteriorly and inferiorly. Such a move can result in obstructive sleep apnea and snoring. The horizontal bar has a telescoping embodiment so that the length of the horizontal bar can be adjusted and fitted snugly between the molars to fit the anatomical distance between molar teeth, which can vary from person to person. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure 52, is attached to the proximal end of the vertical bar 53 and affixed to the lips, which prevents the moving of the device backwards or being accidentally swallowed or aspirated.

The device 220 can also be provided with tubing and connections for supplemental oxygen delivery system 65, 66 that delivers oxygen at the laryngeal inlet 59 at the back of the tongue. It can also have therapeutic agent's delivery tubing with a three-way stopcock and syringe 63 to deliver any therapeutic agents on the middle of the dorsal surface of the tongue 64 to treat pathologic conditions of the tongue and oral cavity. This tubing also delivers anti-halitosis therapeutic agents or local anesthetics to prevent bad breath and to reduce the sensitivity of the tongue if needed.

In addition, the device has two vacuum cups 68, 69 placed on a square or oval metal or plastic plate 67 attached to the vertical bar 53, behind the horizontal bar 54. The vacuum cups are pressed against the hard palate, and the dorsum of the tongue will hold the device and the tongue firmly in position due to creation of vacuum between these two surfaces. This prevents tongue movement posteriorly and inferiorly during sleep due to relaxation of tongue muscles, that causes snoring and obstructive sleep apnea. Accordingly, this embodiment further adds to the effectiveness of the device as an anti-snoring and anti-obstructive sleep apnea device. The vacuum cups' concave surface creates vacuum by pressing them against the hard palate and dorsum of the tongue. Alternatively, dental adhesive can be applied on the concave surface of the vacuum cups 68, 69 to hold the tongue and the device firmly in place tethered to the hard palate.

Figure 12:
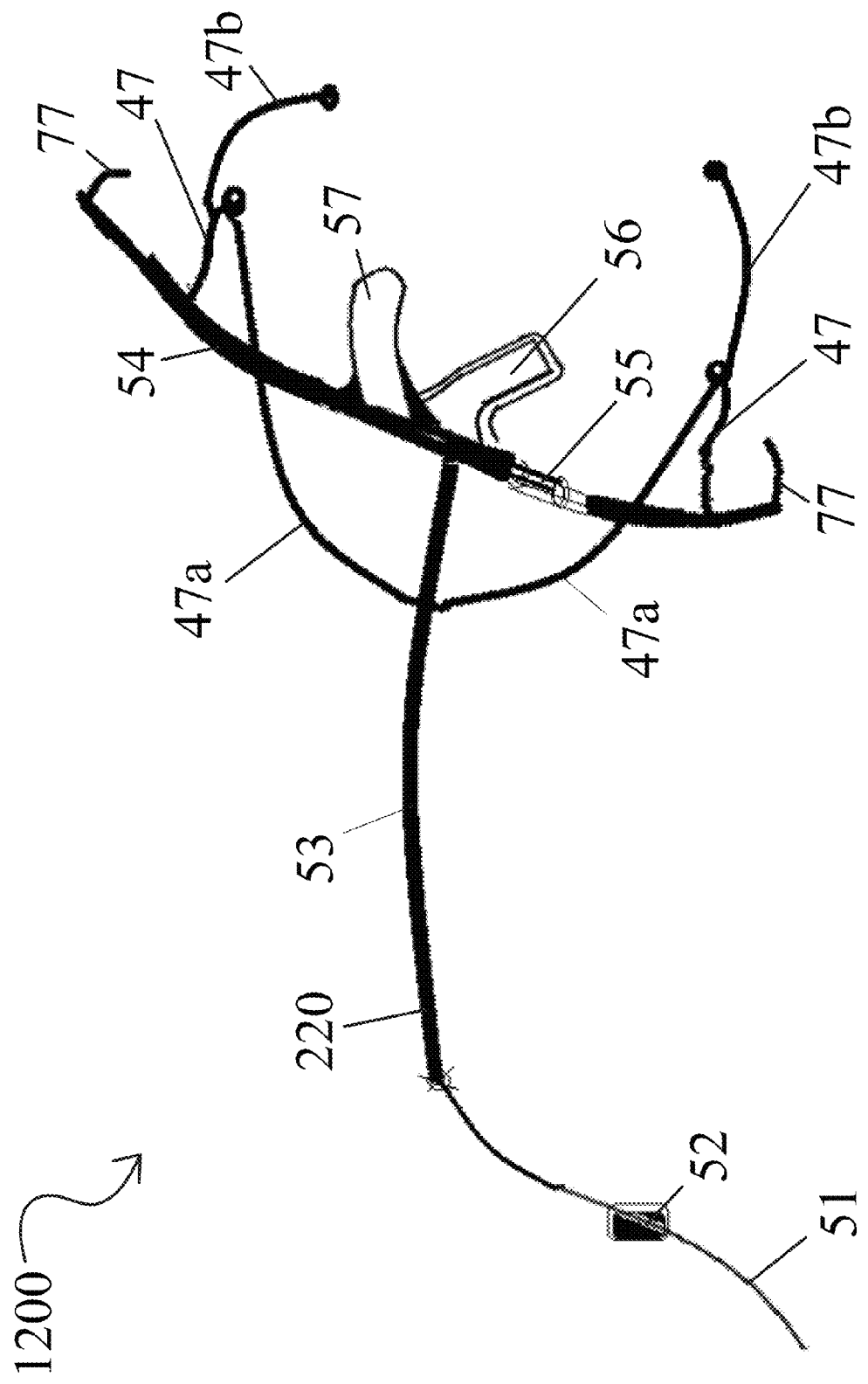
FIG. 12 is the view of the diagram 1200 showing the embodiments used for stopping snoring and obstructive sleep apnea device 220.

FIG. 12 is the view of the diagram 1200 showing the tongue looking from above downwards, having one of the embodiments used for stopping snoring and obstructive sleep apnea device 220. The device is placed in the mouth between the upper and lower retro-molar space 42 as an anti-snoring and anti-obstructive sleep apnea device. It has horizontal bar 56 attached to vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, where as the extension projection 56 hold the tongue forwards, and prevents it sliding posteriorly and inferiorly. Such a move can result in obstructive sleep apnea and snoring. The horizontal bar has telescoping embodiment 55 so that the horizontal bar is fitted snugly between the molars to fit the anatomical distance between molar teeth, which can vary from person to person outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould could also used to hold the horizontal bar in position inserting the cap on the molar teeth instead of vertical extensions peg holders. The anchoring string 51 with hook and loop fabric closure 52, is attached to the proximal end of the vertical bar 53 and affixed to the lips, which prevents the moving of the device backwards or being accidentally swallowed or aspirated.

From the end of the vertical extension 47, two curved round plastic or metal wires 47a and 47b are attached called tongue root holders. They hold the device 220 in fixed position. At the same time, they prevent the movement of the tongue backwards during sleep, which results in obstructive sleep apnea. See the diagram 800 in FIG. 8 how the tongue is incorporated to show how these tongue root holders encircle the root of the tongue and prevent its movement backwards, the tongue held between the horizontal and vertical bar and tongue root holders. Further, they also anchor the tongue between the device's vertical and horizontal bars 53, 54. The tongue root holders 47a, 47b prevent any movement of the flaccid tongue during sleep due to relaxation of tongue root muscles. The tongue root holders can be completely attached to the other end of the device as shown in the diagram or can be partial as shown in the FIG. 8 likened to a sickle shape as seen in the FIG. 8.

Figure 13:
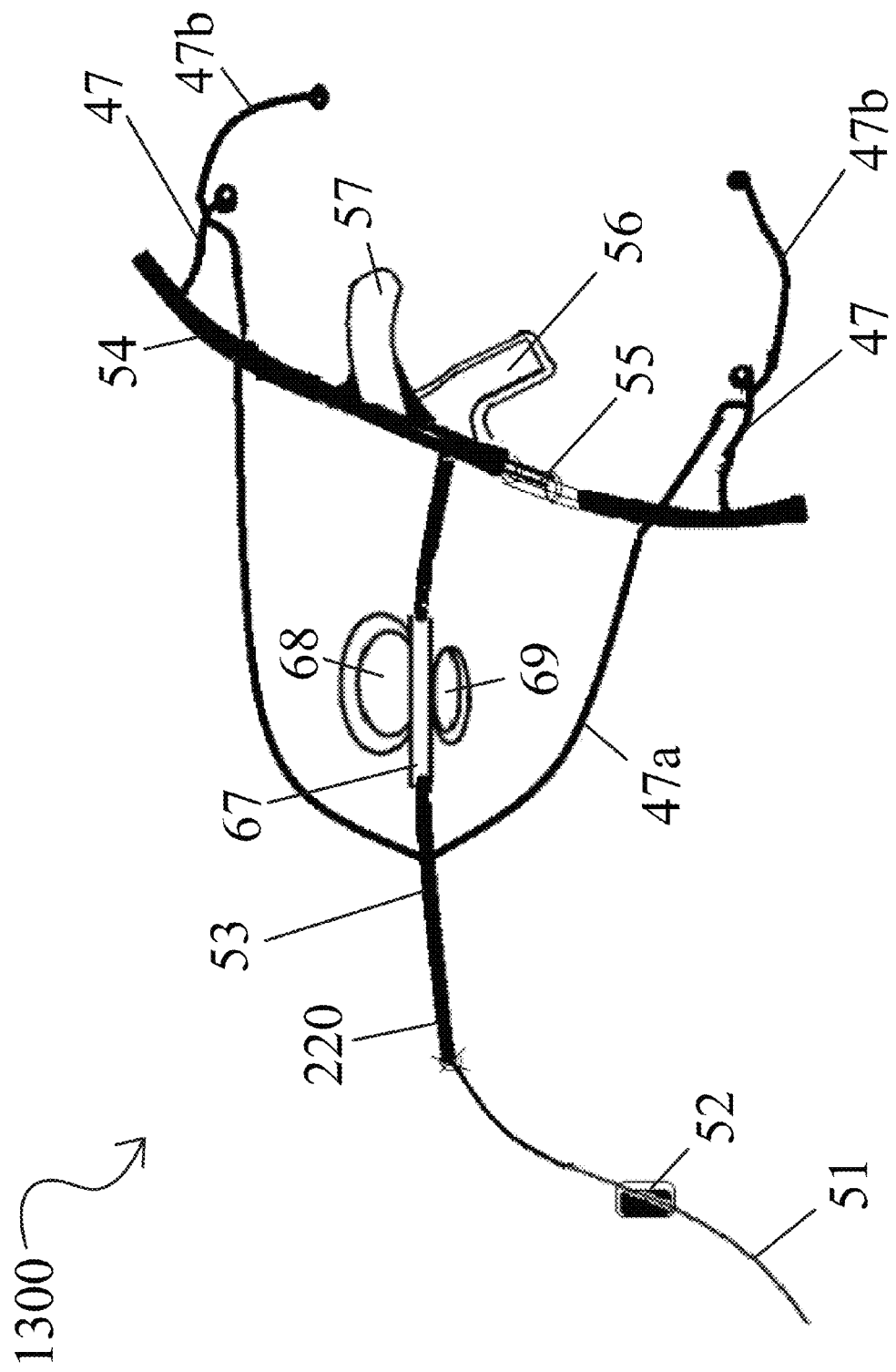
FIG. 13 is the view of the diagram 1300 showing one of the embodiments used for stopping snoring and obstructive sleep apnea device 220.

FIG. 13 is the view of the diagram 1300 showing one of the embodiments used for stopping snoring and obstructive sleep apnea device 220, placed in the mouth in the retro-molar space as described above. It has the horizontal bar 54 attached to the vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, whereas the extension projection 56 hold the tongue forwards, and prevents it sliding posteriorly and inferiorly. Such a move can result in obstructive sleep apnea and snoring. The horizontal bar has telescoping embodiment 55 so that the horizontal bar is fitted snugly between the molars to fit the anatomical distance between molar teeth, which can vary from person to person.

The end of the horizontal bar has two slightly concave Vertical Extensions (pegs) 47, 77—placed about $5/16^{th}$ inches apart located at the end of the device 220. The end of the horizontal bar provided with short vertical peg 77 (not shown in the diagram) compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure 52, is attached to the proximal end of the vertical bar 53 and affixed to the lips, which prevents the moving of the device backwards or being accidentally swallowed or aspirated.

From the end of the vertical extension 47, two curved round plastic or metal wires 47a and 47b are attached called tongue root holders. They hold the device 220 in positions. At the same time, they prevent the movement of the tongue backwards during sleep, which results in obstructive sleep apnea. The 880 diagram incorporates the tongue to show how these tongue root holders encircle the root of the tongue and prevent its movement. Further, they also anchor the tongue between the device's vertical and horizontal bars 53, 54. The tongue root holders 47a 47b prevent any movement of the flaccid tongue during sleep due to the relaxation of tongue root muscles. The tongue root holders can be completely attached to the other end of the device as shown in the diagram or can be partial as shown in FIG. 8.

In addition, the device has two vacuum cups 68, 69 placed on a square or oval metal or plastic plate 67 attached to the vertical bar 53. When the vacuum cups are pressed against the hard palate, the dorsum of the tongue will hold the device and the tongue firmly in position due to the creation of vacuum between these two surfaces. This prevents tongue movement posteriorly and inferiorly during sleep due to the relaxation of tongue muscles that cause snoring and obstructive sleep apnea. Thus, this embodiment further adds to the effectiveness of the device as an anti-snoring and anti-obstructive sleep apnea device. The vacuum cups' concave surface creates a vacuum by pressing against the hard palate and dorsum of the tongue. Alternately, dental adhesive applied on the concave surface of the vacuum cups 68, 69 can hold the tongue and the device firmly in place, tethered to the hard palate.

The anchoring string 51 with hook and loop fabric closure 52 is also provided with this device, and it is attached to the proximal end of the vertical bar 53 and affixed to the lips by hook and loop fabric closure adhesive 42, which prevents the moving of the device backwards or being accidentally swallowed or aspirated. It also holds and provides additional support to prevent the movement of the tongue backwards during sleep and thus prevent obstructive sleep apnea and snoring.

It is important to note that a simple horizontal with vertical bar with tongue root holder's device 220 with small tongue shelf with or without vacuum cups is all that is needed in mild to moderate cases of obstructive sleep apnea syndrome. As the device evolves, further modification and fine-tuning are in order to make the device simple, more effective, and convenient to use for maximum compliance to fit the need of individual patients.

Figure 14:
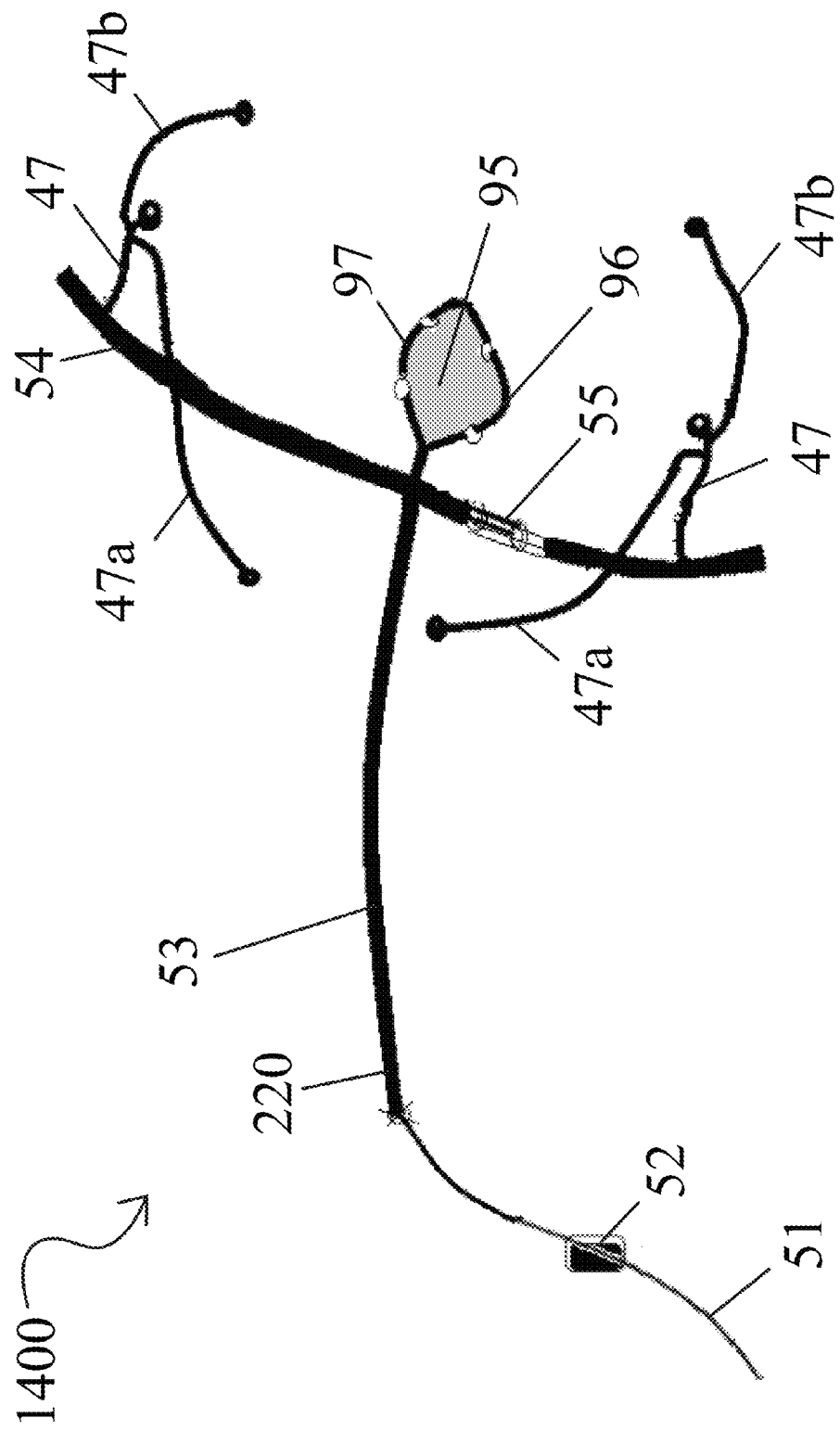
FIG. 14 is the view of the diagram 1400 showing the embodiments used for stopping snoring and obstructive sleep apnea device 220.

FIG. 14 is the view of diagram 1400 showing one of the embodiments used for stopping snoring and obstructive sleep apnea device 220 placed in the mouth in the retro-molar space as described above. It has the horizontal bar 54 attached to the vertical bar 53. The vertical and horizontal bars are slightly concave to fit the convex dorsal surface of the tongue snugly. At the junction of the vertical and horizontal bar, there is round hollow plastic, silicone, or metal ball 95 attached firmly to the junction of the horizontal and vertical bars. This ball has the protrusion of the dorsal aspect 97 that prevents the soft palate meeting tongue or the pharyngeal wall, which prevents snoring. It also has ventral bulge 96, which encounters the dorsum of the tongue. It acts as a mechanical barrier, which prevents the movement of the tongue backwards during sleep and prevents obstructive sleep apnea and snoring.

The end of the horizontal bar has two slightly concave Vertical Extensions (pegs) 47, 77—placed about $5/16^{th}$ inches apart located at the end of the device 220. The end of the horizontal bar provided with short vertical peg 77 (not shown in this diagram) compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure 52, is attached to the proximal end of the vertical bar 53 and affixed to the lips, which prevents the moving of the device backwards or being accidentally swallowed or aspirated.

At the junction of the vertical and horizontal bars, on the middle of the horizontal bar, it has a round plastic or silicone ball 95 instead of metal ball as described above; which has palatine bulge 97 and tongue bulge 96 instead of shelves. The ball can be replaced with a silicone balloon instead, when it is blown, it has the ball bulging 96 and 97, that abuts against the soft palate and dorsum of the tongue and act as mechanical obstacles for soft palate to vibrate and tongue to move back to cause snoring and obstructive sleep apnea. The ball 95 can vary in size depending upon the anatomy of the mouth opening and the size of the opening between the soft palate and dorsum of the tongue. It can be small, medium, or large to fit the size of the oro-pharyngeal opening. The horizontal bar 55 of the device holds both the metal or silicone ball and the tongue in position to increase the effect of the device as an anti-snoring and anti-obstructive sleep apnea device. Provisions for supplemental oxygen and therapeutic agent's delivery is provided.

Figure 15:
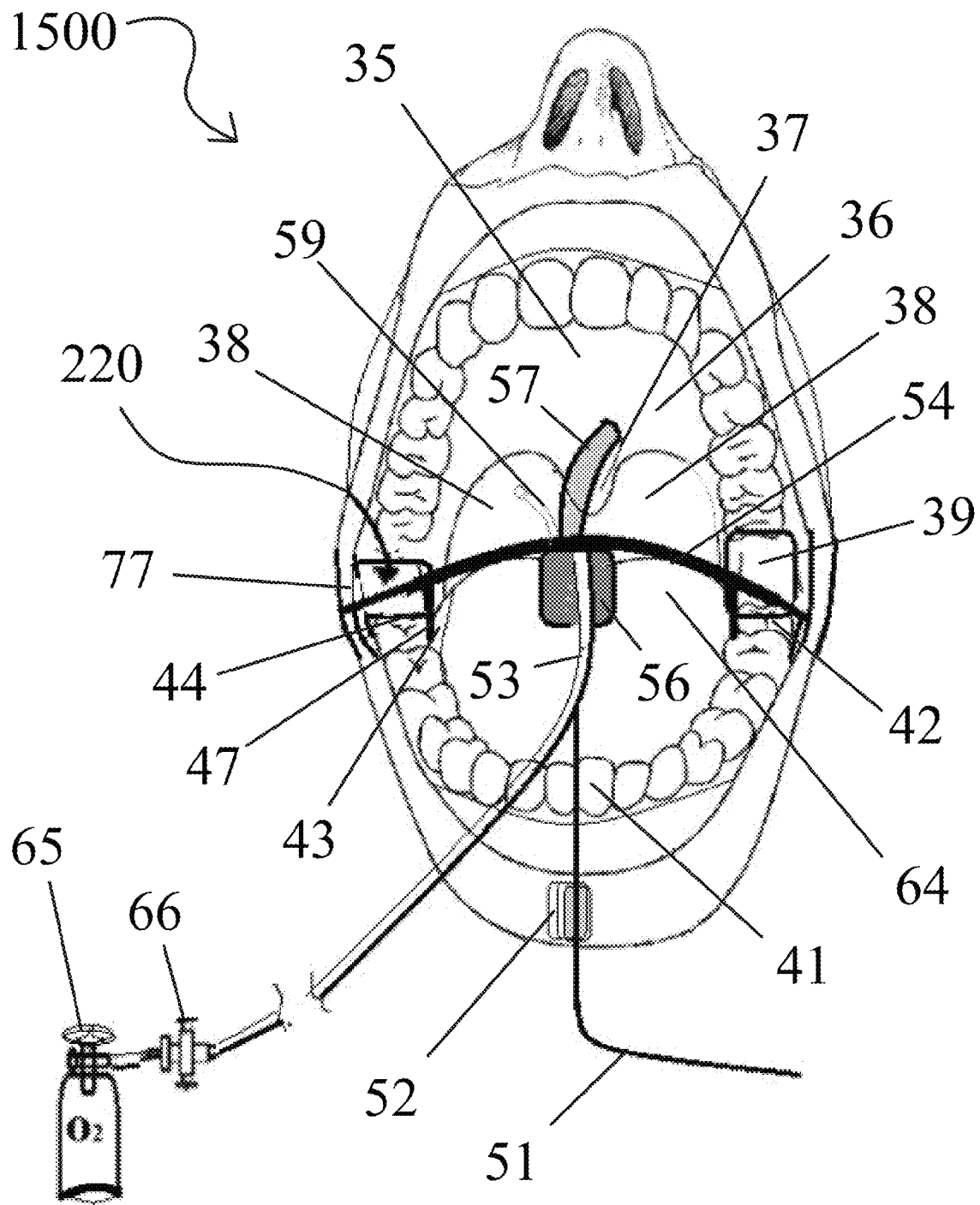
FIG. 15 is the view of the diagram 1500 showing the tongue and palate looked from the front of the fully opened mouth, having one of the embodiments used for stopping snoring and obstructive sleep apnea device 220.

FIG. 15 is the view of the diagram 1500 showing embodiments of this invention device 220 in position in the mouth. The device is in the mouth between the upper and lower retro-molar space as an anti-snoring and anti-obstructive sleep apnea device. Note how the horizontal bar 55 is located at the beginning of the soft palate and the soft palate shelf 57 abuts against the muscle mass of the soft palate 36 to prevent it moving down on the dorsal aspect of the tongue to create snoring and obstructive sleep apnea.

The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders. All the description is the same as FIGS. 6 to 14. The device 220 has all the embodiments described in the above diagrams.

Figure 16:
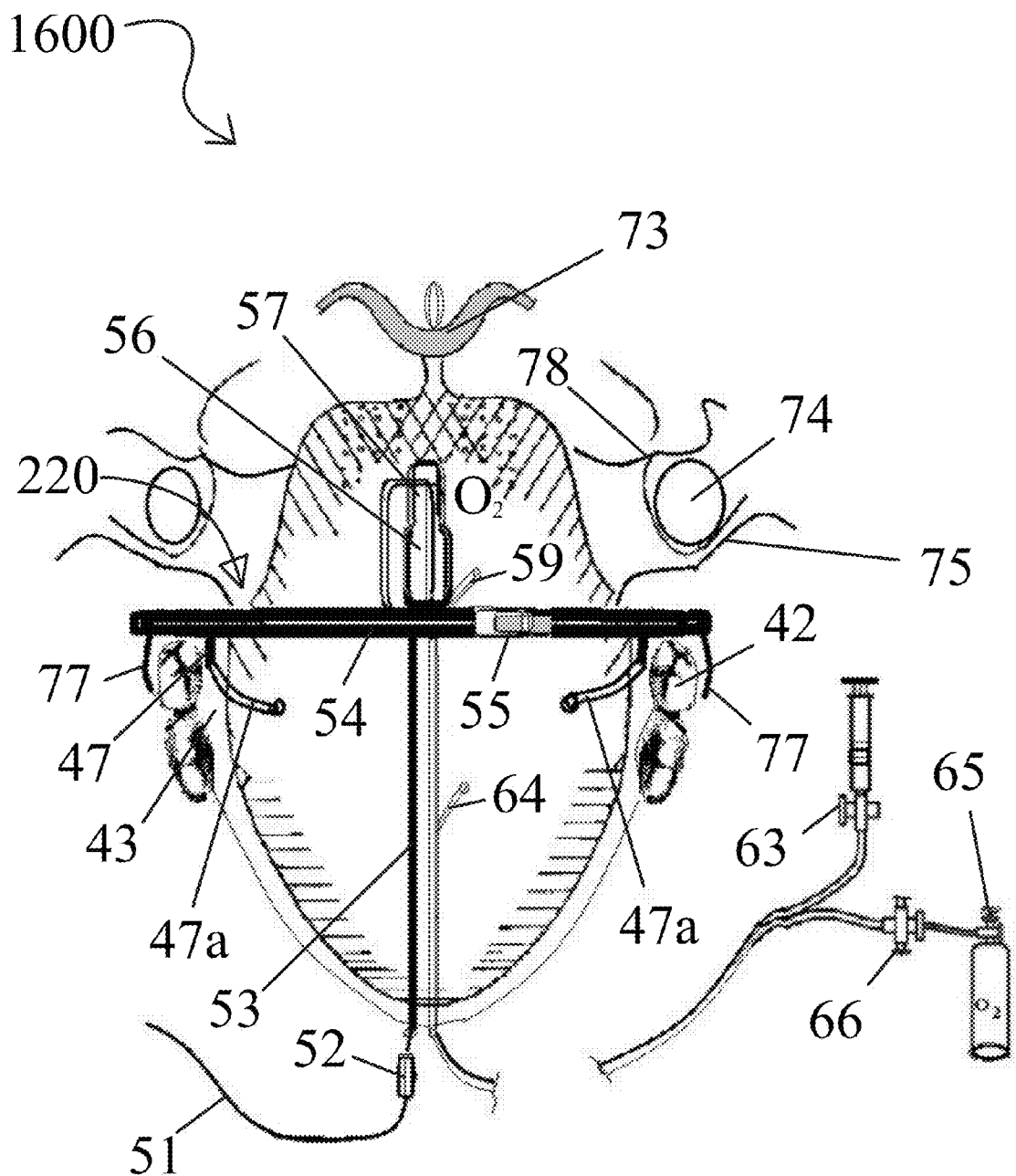
FIG. 16 is the view of the diagram 1600 showing embodiments of this invention device 220 in position in the mouth, used for stopping snoring and obstructive sleep apnea visualized from the top.

FIG. 16 is the view of the photograph 1600 showing the tongue looking from above downwards, with the device 220 used for stopping snoring and obstructive sleep apnea. The device is placed in the mouth between the upper and lower retro-molar space 42 as an anti-snoring and anti-obstructive sleep apnea device. It has the horizontal bar 56 attached to the vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material or thick wires in an oblong square shape. The extension shelf 57 holds the soft palate and the uvula upwards, whereas the extension projection 56 hold the tongue forwards, and prevents it sliding posteriorly and inferiorly. Such a move can result in obstructive sleep apnea and snoring. The horizontal bar has telescoping embodiment 55 so that the horizontal bar is fitted snugly between the molars to fit the anatomical distance between molar teeth, which can vary from person to person. The end of the horizontal bar has two slightly concave Vertical Extensions (pegs) 47, 77—placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure (Velcro®) 52, is attached to the proximal end of the vertical bar 53 and affixed to the lips, which prevents the moving of the device backwards or being accidentally swallowed or aspirated.

It shows various parts of the device 220 in contact with the anatomy of the mouth. The ends of the horizontal bar are in front of the anterior pillars of the tonsils 74, 75, farther away from the posterior pillar 78 of the tonsil. It is located exactly behind the molar teeth 42 and vertical concave studs 47 situated in the space 43 between the gums and the lateral border of the tongue.

There is sufficient space between the upper and lower jaws molar teeth, there are pterygoglossus and pterygo-mandibular ridge (FIG. 17 #80) in front of the anterior pillars of the tonsil 75. It is important to note that the root of the tongue muscles, including those which attach to the tongue in all direction, converge at the root, at the inter molar regions of the mouth making this device 220 effective in restraining the movement of the tongue and prevent the obstructive sleep apnea.

The device 220 can also be provided with tubing and connections for supplemental oxygen delivery system 65, 66 that delivers oxygen at the laryngeal inlet 59 at the back of the tongue. It also has therapeutic agent's delivery tubing with a three-way stopcock and syringe 63 to deliver any therapeutic agents on the middle of the dorsal surface of the tongue 64 to treat pathologic conditions of the tongue and oral cavity. This tubing also delivers anti-halitosis therapeutic agents or local anesthetics to prevent bad breath and to reduce the sensitivity of the tongue if needed.

Figure 17:
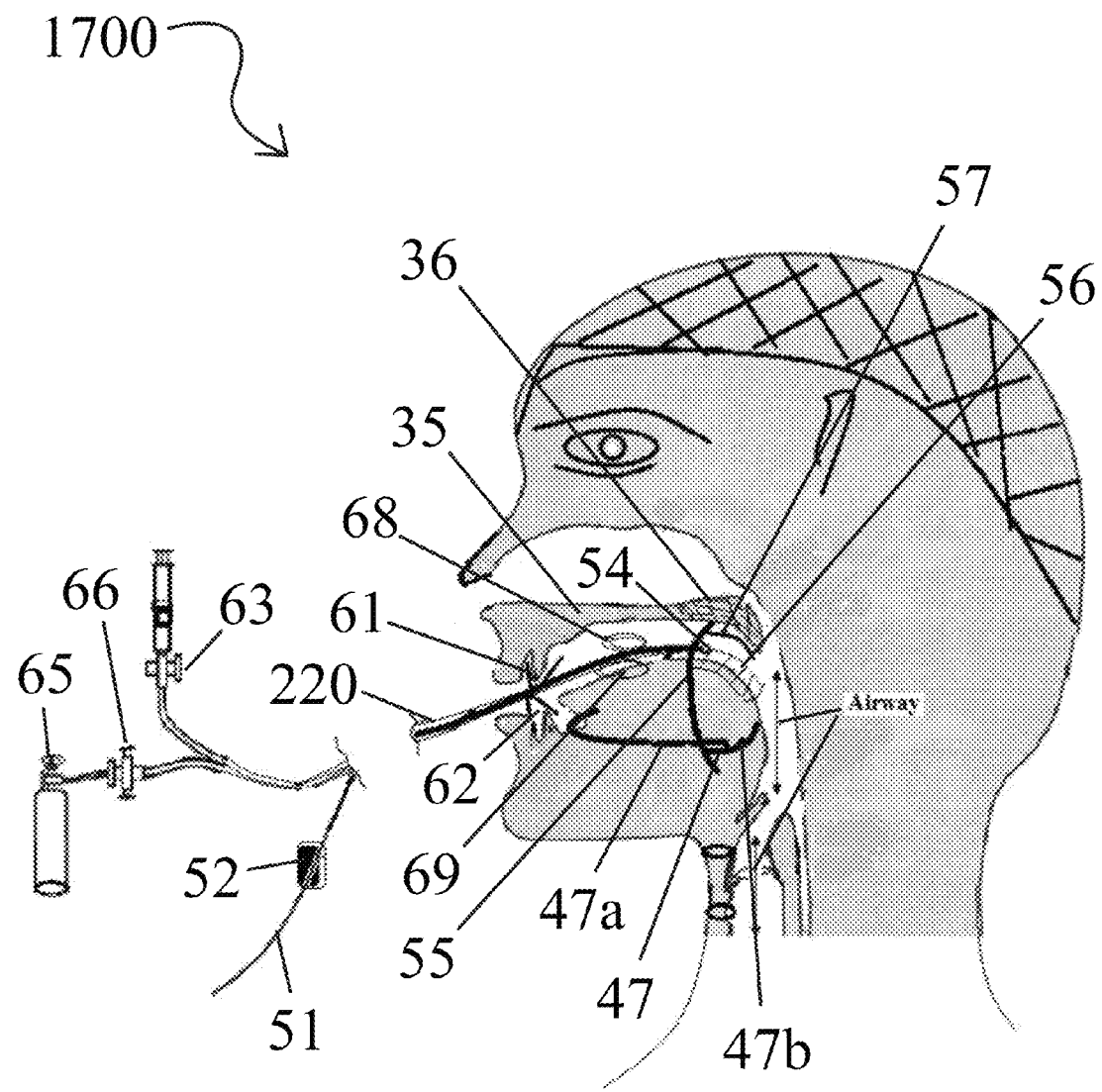
FIG. 17 is the view of the photograph 1700 of the mouth open showing one of the embodiments in position in the mouth used for stopping snoring and obstructive sleep apnea device 220.

FIG. 17 is the view of the diagram 1700 showing embodiments of this invention device 220 in position in the mouth. The device is in the mouth between the upper and lower retro-molar space as an anti-snoring and anti-obstructive sleep apnea device. Note how the horizontal bar 55 is located at the beginning of the soft palate and the soft palate shelf 57 abuts against the muscle mass of the soft palate 36 and uvula to prevent it moving down on the dorsal aspect of the tongue to create snoring and obstructive sleep apnea. All the description is the same as FIGS. 6 to 14. The device 220 has all the embodiments described in the above diagrams. It shows the incisor teeth sockets 61, 62, and the oxygen delivery system 65, 66, with therapeutic agents' delivery canula 63. The vacuum cups 68, 69 are located immediately below the hard palate 35 so that they can hold the device 220 and the tongue firmly without allowing for any movement backwards. Note how the soft palate and uvula holding plate 57 and the tongue holding plate 56 act as a shelf to hold the tongue and the soft palate in place and act as an anti-snoring and anti-obstructive sleep apnea device. Arrows points to the route of respiratory air movement with the use of this device.

From the end of the vertical extension 47, two curved round rigid preformed plastic or metal wires 47a and 47b are attached called tongue root holders or restrainers. They hold the device 220 in position, and at the same time prevent the movement of the tongue backwards during sleep, which is the root cause of the obstructive sleep apnea with or without snoring. The diagram incorporates the tongue root, to show how these tongue root holders or restrainers encircle the root of the tongue, thus hold back, hold down, pin down, confine, and prevent it moving backwards. Further, they also anchor the tongue between the device's vertical and horizontal bars 53, 54. The tongue root holders 47a, 47b prevent any movement of the flaccid tongue during sleep due to the relaxation of tongue root muscles as shown in the FIG. 20. The tongue root holders 47a and 47b attached to the other end of the device 47 as shown in the diagram 12 can be in full circle, or can be partial as shown in this FIG. 8 likened to the shape of a sickle. They hold the tongue in fixed position without much room to wiggle around during sleep when the muscles of the tongue lose their tonicity and become flaccid.

Figure 18:
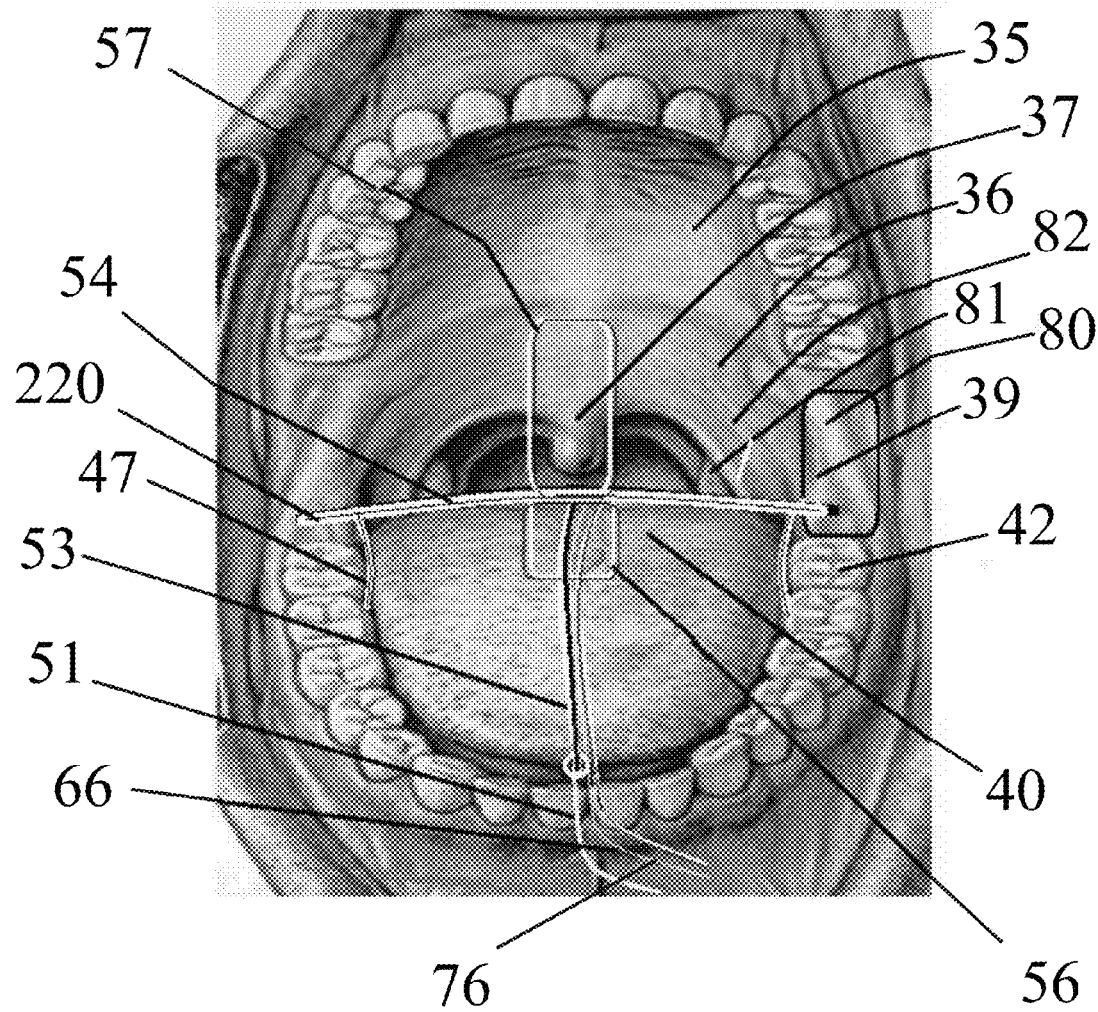
FIG. 18 is the photographic presentation 1800 showing how the inventive device to treat anti-snoring and anti-obstructive sleep apnea device 220 is placed in the mouth and its anatomical location in the mouth.

FIG. 18 is the view of the actual photograph 1800 of the mouth wide open, showing the device 220 used for stopping snoring and obstructive sleep apnea placed in the mouth in the retro-molar space 39. It has the horizontal bar 54 attached to the vertical bar 53. The vertical and horizontal bars are slightly concave to fit the convex dorsal surface of the tongue snugly. At the junction of the vertical and horizontal bar, there are two metal or plastic extensions (shelves) 56, 57 made up of plates of metal, plastic, composite material, or thick wires in an oblong square or oval shape. The extension shelf 57 holds the soft palate and the uvula upwards, whereas the extension projection 56 hold the tongue forwards, and prevents it sliding posteriorly and inferiorly. Such a move if not prevented, results in obstructive sleep apnea and snoring. The horizontal bar has a telescoping embodiment so that the horizontal bar is fitted snugly between the molars to fit the anatomical distance between molar teeth, which can vary from person to person. The end of the horizontal bar has two slightly concave Vertical Extensions (pegs) 47, 77 placed about $5/16^{th}$ inches apart located at the end of the device 220. The end of the horizontal bar provided with short vertical peg 77 compared to the peg 47, which is longer, and it is located outside the molar teeth to accommodate molar teeth between the 47 and 77 pegs or extensions. The space also accommodates the gum at the retro molar space. These two embodiments hold the device 220 in position without oscillating movements. They also help to prevent the tongue movement backwards. The molar negative cap mould used to hold the horizontal bar in position inserting the cap on the molar teeth instead of vertical extensions peg holders.

The anchoring string 51 with hook and loop fabric closure is attached to the proximal end of the vertical bar 53 and affixed to the lips, which prevents the moving of the device backwards or being accidentally swallowed or aspirated.

This photograph shows the pterygo-glossus ridge 80 located in the post-molar space 39, palato-glossus and styloglossus muscles 82, which form the anterior pillar 81 of the tonsil. Note that the horizontal bar when placed in the moth behind the molar teeth 42 is located at the junction of the hard 35 and soft palate 36, the end of the hard palate and beginning of the soft palate. The device is in the ideal position to stimulate and hold the soft palate 35 with palatine shelf 57 and tongue shelf 56 to prevent snoring and obstructive sleep apnea. The oxygen delivery tubing 66 can connect the oxygen delivery system to the rest of the vertical bar and other embodiments shown in the FIG. 10. The rest of explanation is the same as FIGS. 6-10 described above.

Figure 19:
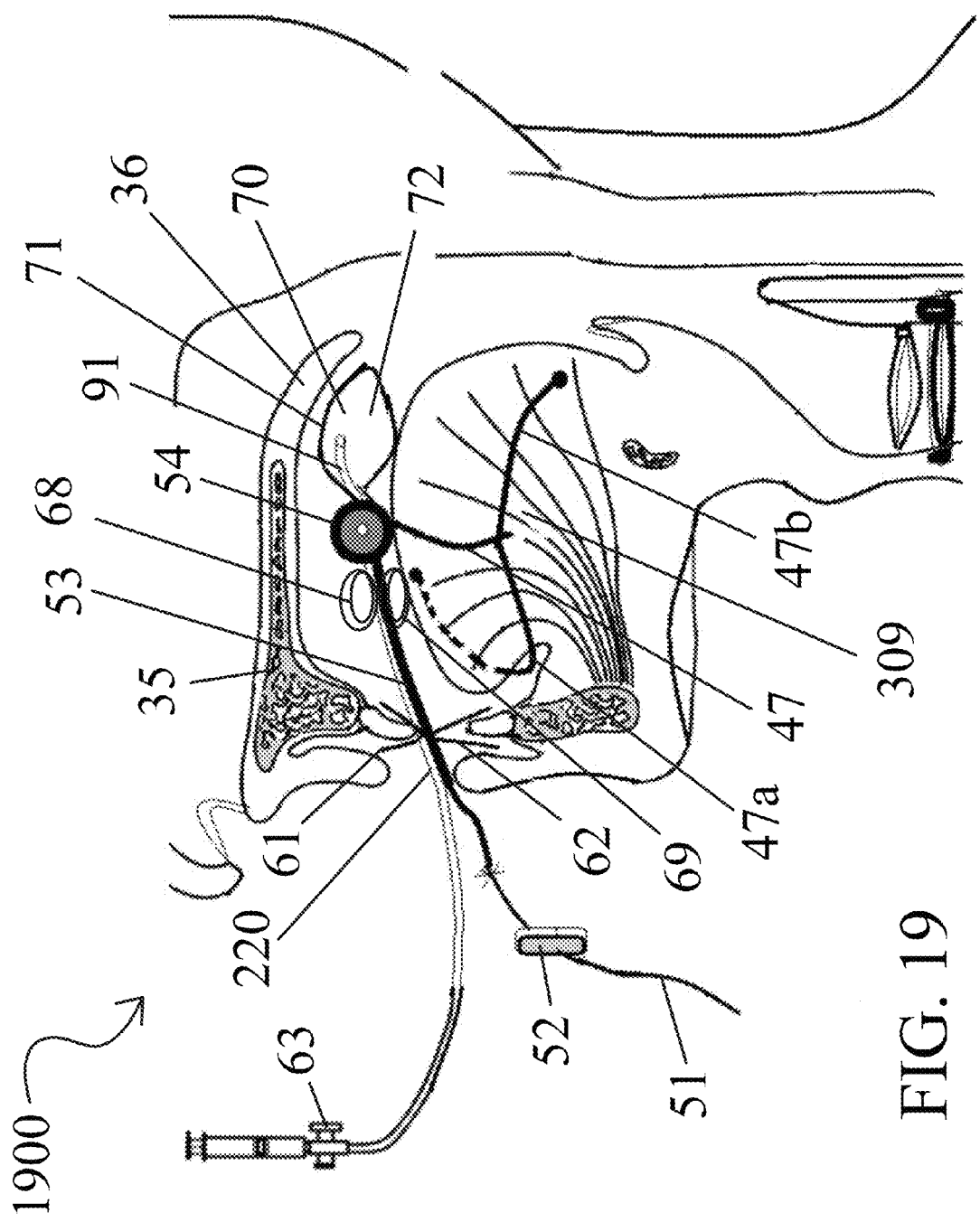
FIG. 19 is the view of the diagrammatic presentation 1900 of the mouth showing one of the embodiments used for stopping snoring and obstructive sleep apnea device 220 in position.

FIG. 19 is the diagrammatic presentation 1900 showing the device 220 placed in the mouth in the retro-molar space as described above. It has the horizontal bar 54 attached to the vertical bar 53. The vertical and horizontal bars are slightly concave to fit the convex dorsal surface of the tongue snugly. At the junction of the vertical and horizontal bar, there is oblong rigid silicone balloon 70 attached firmly. It has a bulge 71 that abuts against the soft palate 36 and prevents vibration and stops snoring. The balloon also has ventral bulge 72 that abuts against the dorsum of the tongue and prevents its backward movement, thus preventing obstructive sleep apnea. The balloon expanded with liquid or gel from external syringe 63 delivered inside the balloon at the distal end 91 catheter through a connecting delivery tubing. The size of the balloon is adjusted by increasing or reducing the filling fluid from the external source syringe according to the convenience of the patients. The extension shelf 71 holds the soft palate and the uvula upwards, whereas the extension projection 72 hold the tongue forwards, and prevents it sliding posteriorly and inferiorly. Such a move if not prevented results in obstructive sleep apnea and snoring. The horizontal bar has telescoping embodiment 55 as shown in FIGS. 8-14, so that the horizontal bar breadth can be adjusted and so that the device 220 is fitted snugly between the molars. It is important to provide it because the anatomical distance between molar teeth can vary from person to person. The anchoring string 51 with hook and loop fabric closure 52, is attached to the proximal end of the vertical bar 53 and affixed to the lips, which prevents the moving of the device backwards or being accidentally swallowed or aspirated.

This device 220 incorporates V shaped incisor sockets 61, 62, at the proximal end of the vertical bar 53 to hold the device in position and prevent its movement backwards between the teeth. They also prevent the movement of the lower jaw against the fixed upper jaw backwards during sleep to prevent obstructive sleep apnea.

From the end of the vertical extension 47, two curved round rigid preformed plastic or metal wires 47a and 47b are attached called tongue root holders encircling the muscles of the root of the tongue. They hold the device 220 in position and at the same time prevent the movement of the tongue backwards during sleep, which is the root cause of the obstructive sleep apnea. The diagram incorporates the tongue to show how these tongue root holders or restrainers encircle the root of the tongue, especially the genioglossus muscle 309 which form the bulk of the root of the tongue, and thus hold back, hold down, pin down, confine, and prevent it moving backwards. Further, they also anchor the tongue between the device's vertical and horizontal bars 53, 54. The tongue root holders 47a, 47b prevent any movement of the flaccid tongue during sleep due to the relaxation of tongue root muscles as shown in the FIG. 3. The tongue root holders can be attached to the other end of the device as shown in diagram 12 in full circle, or can be partial as shown in this FIG. 8 likened to the shape of a sickle.

FIG. 20 is the diagrammatic presentation 2000 showing the muscles involved in the movement of the tongue, and root of the tongue involved in causing obstructive sleep apnea. It shows Stylogolssus muscle 301, Ramus of the Mandible 302, Styloid processes 303, Stylo-hyoid muscle 304, Hyo glossus muscle 305, Styolo thyroid muscle 306 with stylo hyoid ligament 315 behind it attached to the posterior end of the hyoid bone 307, Thyroid cartilage 308, Genio glossus muscle 309, Genio hyoid muscle 310, Genoid tubercle 311, and Mandible 312.

The tongue is made up of five intrinsic muscles: superior, inferior, longitudinal, transverse, and vertical muscles not attached to any bone, and four extrinsic muscles: genio, hyo, stylo, and palato glossus muscles that attach to bones as shown in the diagram. The skeletal muscles in the tongue are arranged in three different planes. This allows the tongue to perform a number of complex movements in every direction. While asleep in the supine position, all the tongue muscles relax; the muscle mass of the tongue moves back due to weight and gravitation pull, resulting in obstruction of the airway causing snoring and obstructive sleep apnea (FIGS. 1, 2, 3). This inventive device along with tongue root holders prevents obstructive sleep apnea and snoring.

Maintaining the proper tone of these muscles is important for prevention of snoring and the obstructive sleep apnea (OSA) during sleep. The dorsal surface of the tongue with intrinsic muscles 314 without any bony attachment moves en-mass backwards and downwards towards the oral and laryngeal pharynx and along with other muscles is responsible for the obstruction of the airway resulting in obstructive sleep apnea (see FIGS. 2, 3) when these muscles lose tone during sleep. However, all the muscles shown in the diagram including suprahyoid and infrahyoid (not shown) muscles play a role in obstructive sleep apnea. However the genioglossus 309 plays a major role in the obstructive sleep apnea when it is relaxed (because of its mass and insertion into the ventral aspect of the tongue, which forms the main body of the root of the tongue). It allows the tongue to move backwards during sleep. The invention describe herein prevents the movement of the tongue due to increased tone of the tongue muscles and prevents snoring also due to the tonic palatine muscles. Thus, it prevents the obstructive sleep apnea by mechanical block of the root of the tongue through the projections 47a and 47b.

The palate forms the roof of the mouth. It made up of two regions: the hard palate in front and the soft palate behind (FIGS. 3, 4, 16, 17, 18, 19). The hard palate is formed by the palatine processes of the maxillae in front, and horizontal plate of the palatine bone behind. The horizontal plates of the palatine bones behind gives origin to the palatine muscles and continues with the soft palate. The soft palate plays an important role in snoring and to some extent in the production of obstructive sleep apnea. The soft palate is suspended from the posterior border of the hard palate. It extends downwards and backwards between the oral and nasal parts of the pharynx. It consists of a mucous membrane enclosing an aponeurosis, muscular fibers, vessels, nerves, lymphoid tissue, and mucous glands. Its superior border is attached to the posterior margin of the hard palate, and its sides are blended with the pharynx and its muscles. Its inferior border is free, which contributes to snoring attributable to the vibration result of restricted airflow. The uvula is a diminutive conical form (musculus uvulae) suspended from the middle of its lower (posterior) border and has two curved borders of mucous membrane (see FIGS. 15, 17, 18, 19). It contains muscular fibers (palato-pharynges and palatoglossal arch) and extends laterally and downwards from each side of the base of the uvula. A fibrous palatine aponeurosis lamella is attached to the posterior border of the hard boney palate and to the inferior surface of the hard palate behind the palatine crest that supports the palatine muscles and gives strength to the soft palate. The metal shelf, inflated balloon and silicone or metal ball described in this present invention prevents the soft palate movement downwards during sleep to create snoring and prevent obstructive sleep apnea.

The flexible skeleton for the soft palate movement is due to the aponeurosis of the tensor palati muscle responsible for snoring. There are five pairs of palatine muscles of the soft palate that are involved in the movement of the palate and uvula, that participate in the production of snoring. They are 1. tensor palati, 2. levator palati, 3. Palatopharyngeus (at the posterior pillar of the tonsil) of the upper surface, 4. uvular muscles within the upper surface, and 5. Palatoglossus (at the anterior pillar of the tonsil) from the lower surface. The thin muscles of the soft palate lose their tone during sleep, lengthen in size, and move toward the pharynx and the back of the tongue, and act as a resonating instrument like a drum or thick string reverberating with the passage of air during respiration, resulting in snoring during sleep. The flexible skeleton for the soft palate is provided by the aponeurosis of tensor palati muscle on which the soft palate moves when relaxed during snoring. The horizontal bar of the device 220 is situated next to this aponeurosis and provides the maximum effect to maintain its tone to prevent the snoring.

Snoring, hypopnea and obstructive sleep apnea are caused by the vibrating soft palate, the soft tissue of the nasal, oral and laryngeal pharynx; along with the relaxed tongue moving backwards towards the oral and laryngeal pharynx; thus, blocking of the air passageway through the pharynx. Snoring is an inspiratory sound, which arises in the course of a person's sleep, is due to the narrowing of the naso-oro- and laryngo-pharyngeal airway, and is mostly produced by the soft palate. The sounds of snoring are generated by vibration of soft tissues of the oropharynx which involves the soft palate, uvula, tongue, lips, the posterior faucial pillars of the tonsils, pharyngeal folds, posterior, lateral pharyngeal wall and epiglottis in the upper airway. Preventing the movement of the soft palate by mechanical means, muscles of the tongue and pharyngeal wall will prevent the snoring and obstructive sleep apnea as described in this invention.

Preparation of the Patient and Employing the Device

Examine the patient thoroughly, especially the tongue, oropharyngeal area, nose, and throat for any medical and mechanical conditions that can predispose to snoring with or without obstructive sleep apnea. If there is a contributing factor found, and correctable, the patient is advised to seek medical help to correct the issues when using the device for treatment of snoring and obstructive sleep apnea. If the patient has undergone sleep studies to diagnose sleep apnea, refer to the report obtained to gauge the severity of the OSA. The patient is advised to stop smoking, to avoid the use of narcotics, sleeping medications, hypnotics, sedative, sleep causing antihistamines, and alcohol before going to bed. To avoid food regurgitation, which can add to the pathophysiology of OSA, the patient must eat a moderate dinner about 3-4 hours before going to bed. A patient should avoid watching the TV and sleep in a quiet room without any external disturbances that can affect sleep. The patient is also advised to use stomach acid production blockers (antacids) to prevent GERD and to prevent regurgitation of the stomach contents which can cause airway problems including aspiration pneumonitis.

The following advice is given before use of anti snoring and obstructive sleep apnea devices such as 1. Brush the teeth, 2. Use floss to clear the gums. 3. Use tongue scraper to clean the tongue of any coating. 4. Use a mild mouth antiseptic wash.

Soak the device in an antiseptic and coat it with lubricant if needed, (using an oily coating which is not toxic such as olive oil). If the device is not tolerable due to sensitivity, the patient may have to use local anesthetic lozenges, which are available over the counter. Our experiments with human subjects showed that the device is tolerated without gagging and without the use of local anesthetic spray. If still difficult to use the device due to sensitivity of the oropharyngeal passages, get local anesthetic jelly or spray (Citanest™ spray) through your physician or used astringent lozenges. Wait until the local anesthetic takes effect and then position it in the mouth. Avoid eating food or drinking if local anesthetic spray is used until it wears off.

Use a well-lighted mirror to position the device to place the soft palate elevator shelf splint appropriately at the correct position in contact with the oral undersurface of the soft palate and uvula. It will facilitate how deep you need to pass device 101 past the tongue and back of the tongue. Make sure the front end of the device 220 is tied to a string provided and attached to the lips with hook and loop fabric closure so that it will not be accidentally swallowed while sleeping. Please use only when needed. Habitual use of the device repeatedly will reduce or eliminate the gag reflex completely with no need to use local anesthetics. Keep the device immersed in antiseptic mouthwash and wash in clean warm water before placement. If oxygen supplementation is needed in pulmonary compromised patients, use an oxygen concentrator or 100% oxygen from the cylinder and keep the flow to the minimum required levels so that it does not disturb sleep.

Insert the device at the post molar space 39, 44 to prevent snoring and close the jaw. For snoring with obstructive sleep apnea, the tongue shelf or splint restrainer 57, 56 carefully positioned properly to prevent the tendency of the flaccid tongue falling or moving posteriorly and inferiorly to cause obstruction to the upper respiratory passages, which causes snoring and obstructive sleep apnea. The only way to prevent the tongue falling back from the floor of the mouth is by mechanical obstruction to prevent the flaccid tongue move backwards during sleep (especially in supine position) provided by our inventive device. The tongue root holders 47a and 47b prevent the movement of the tongue backwards. First use the device 220 without these tongue root holders, embodiment and test if it prevents snoring and obstructive sleep apnea. If it does not, then add the device 220 that incorporates tongue root holders 47a and 47b.

If there is no OSA, the device without the back tongue shelf splint 56 to prevent the movement of the tongue against the pharyngeal wall need not be incorporated in the device and used.

The anti snoring and obstructive sleep apnea device may be made of thermoplastic or elastomeric resin or synthetic plastic or silicone resins with or without metal component such as stainless steel, aluminum, and copper rods added to strengthen the composite materials and add moldability to the user's mouth. It should not be too rigid, must be soft, may be made up of silicone, it must be malleable to prevent trauma to the tongue, retro-molar space, and palate with nightlong use. The device must be made of a non-allergic, hypo allergic, non reacting, non-toxic easy to clean material. The color of the device can also vary. In the morning, remove the device, wash with soap and water, and store in a dry place or immerse in mouth wash solution. It may take time to get used to sleeping with the device. As one used, it become a second nature to use it.

Advantages of the Current Anti Snoring and Anti Obstructive Sleep Apnea Invention One advantage of the present invention is that it is available for anti-snoring and OSA therapies and has an external and internal oral device to reduce or eliminate snoring with or without obstructive sleep apnea during sleep.

An added benefit of the present invention is that it provides for an anti-snoring and OSA device that is easily self-adjustable and does away with the need for professional and laboratory assistance or clinician fabrication.

Another benefit of using this invention is that it has provision for supplemental oxygen for those who have severe pulmonary diseases needing high concentration of supplemental oxygen to prevent any adverse health effects due to OSA hypoxia during sleep.

Yet another advantage of the present invention is that it provides for an anti snoring and OSA combined device fabricated from a thermoplastic material (elastomeric resin) with or without metal components, which can be easily shaped to fit the anatomy of the oral cavity, tongue, and the soft palate.

An extra benefit of the present invention is that it provides for an anti snoring and OSA combined device, which is moldable after immersion in boiling water so that it can be adapted by the user to have a comfortable and individualized fit.

An additional benefit of the present invention is that it provides for an anti-snoring and OSA device coated with therapeutic agents that prevent and treat bad breath and are used to treat the disease afflictions of the tongue and palate. The therapeutic agents can be delivered through the three way stopcock and syringe provided in the device after placement of the device before going to sleep.

An additional benefit of the present invention is that it provides for an anti-snoring and OSA device that has an intra oral dental overlay structure—incisors teeth receptacles or pockets used to displace the lower jaw to the comfortable level at the same time it supports the tongue against the user's palate to keep the palate from reverberating during mouth breathing to prevent snoring and OSA by the user.

A further advantage of the present invention is that it provides for an anti snoring and OSA device which can be easily used, stored, cleaned, and mass produced economically to make it affordable for millions who suffer from snoring with or without obstructive sleep apnea.

A further advantage of the present invention is that it provides for an anti snoring and OSA device with vacuum cups to hold the device tethered to the hard palate and the tongue.

A further advantage of the present invention is that it provides for an anti obstructive sleep apnea device with tongue root holders modality to prevent the backward movement of the tongue.

Numerous modifications; alternative arrangements of steps explained and examples given herein may be devised by those skilled in the art without departing from the spirit and the scope of the present invention. The appended claims are intended to cover such modifications and arrangements.

Thus, the present invention has been described above with particularity and detail in connection. This is presently deemed to be the most practical and preferred embodiment of the invention. It will be apparent to those of ordinary skill in the art that numerous modifications, including, but not limited to, variations in size, materials, shape, form function, and manner of procedure, assembly, and the use may be made. The preferred embodiment of the present invention has been described. It should be understood that various changes, adaptations, and modifications may be made thereto. It should be understood, therefore, that the invention is not limited to details of the illustrated invention. This method can be used to treat snoring with or without obstructive sleep apnea and prevent the health hazards associated with the conditions. The preferred embodiments of the present invention have been described. This should be understood, therefore, that the invention is not limited to details of the illustrated invention examples. Other features and advantages of the present invention will become apparent to one with skill in the art upon examination of the descriptions and drawings. It is intended that all such additional features and advantages be included herein within the scope of the present invention, as defined by the claims.

What is claimed is:

1. An anti-snoring and anti-obstructive sleep apnea oral device disposed in a retro molar space and between a last molar tooth of an oral cavity comprising:
   a. a horizontal bar placed in a retro molar space behind molar teeth, between said molar teeth between an upper and lower jaw;
   b. a vertical bar attached to a middle portion of said horizontal bar extending along a length of a tongue, shaped to fit a dorsal surface of said tongue;
   c. a first slightly concave shelf attached at a junction of said vertical and horizontal bar adapted to abut against a soft palate and an uvula wherein movement is prevented;
   d. a second slightly concave shelf attached at said junction of said vertical and horizontal bar adapted to abut against a dorsal surface of said tongue; wherein backward movement of said tongue is prevented therein preventing obstructive sleep apnea;
   e. a vertical peg disposed on both end portions of said horizontal bar adapted to fit between said molar teeth and gums of said retro molar teeth and a lateral border of said tongue wherein said device in firmly held in place;
   f. a first curved malleable metal bar disposed from a tip of said vertical peg, extending anteriority to cover at least a portion of a root of a tongue undersurface wherein movement is prevented; and
   g. a second curved malleable metal bar disposed from said tip of said vertical peg to a posterior part of said root of said tongue to prevent its backward movement.

2. The anti-snoring and anti-obstructive sleep apnea device according to claim 1, wherein said oral device portion is custom fitted to match a user's oropharyngeal tongue anatomy and pathophysiology.

3. The anti-snoring and anti-obstructive sleep apnea device according to claim 1 further comprising: a string attached to a distal end of said vertical bar wherein said string is attached using a hook and loop fabric closure adhesive attachment to a pair of lips outside a mouth to prevent an accidental swallowing and aspiration of the device while at the same time holding the tongue and device firmly in the mouth.

4. The anti-snoring and anti-obstructive sleep apnea device according to claim 1 further comprising:
   a) a plate portion centrally disposed on said vertical bar in front of said horizontal bar;
   b) a first suction cup disposed on an upper and a second suction cup disposed on a lower surface of said plate portion wherein said first and second suction cups removably hold said oral device to said dorsal surface of said tongue;
   c) wherein said first and second suction cups hold said oral device portion to said dorsal surface of said tongue tethered to a hard palate preventing the tongue from sliding backwards to prevent obstructive sleep apnea; wherein said first and second suction cups are adapted to hold the tongue on the hard palate and the tongue.

5. The anti-snoring and anti-obstructive sleep apnea device according to claim 1 further comprising:
   a) a plurality of oxygen delivery exits disposed on a posterior portion of said oral device portion proximal to a laryngeal airway;
   b) an oxygen delivery tubing portion in conjunction with said oxygen delivery exits and oxygen source, wherein hypoxia is prevented, especially in pulmonary compromised patients; and
   c) an external supplemental oxygen source connected to said oxygen delivery tubing.

6. The anti-snoring and anti-obstructive sleep apnea device according to claim 1 further comprising;
   a) an incisor tooth socket;
   b) said incisor tooth socket having a "V"-shaped configuration, whereby an incisor tooth fits within said incisor tooth socket; wherein said tooth socket prevents a lower jaw and the tongue sliding back during sleep to cause obstructive sleep apnea.

7. An anti-snoring and anti-obstructive sleep apnea device in according to claim 1 further comprising an injection canula with three-way stopcock to deliver at least one of an antibiotics, antiseptics, local anesthetic or therapeutic agent to the surface of the tongue, palate and oral cavity.

8. The anti-snoring and anti-obstructive sleep apnea device according to claim 1, wherein said oral device portion is made of elastomeric resin, moldable thermoplastic, synthetic, semi synthetic, plastic, metallic and composite non toxic, non-reacting material.

* * * * *